(12) United States Patent
Nilsson

(10) Patent No.: US 9,150,682 B2
(45) Date of Patent: Oct. 6, 2015

(54) MODIFIED POLYMER COMPOSITIONS, MODIFICATION PROCESS AND FREE RADICAL GENERATING AGENTS FOR I.A. WIRE AND CABLE APPLICATIONS

(75) Inventor: Daniel Nilsson, Gothenburg (SE)

(73) Assignee: Borealis AG, Vienna (AT)

( * ) Notice: Subject to any disclaimer, the term of this patent is extended or adjusted under 35 U.S.C. 154(b) by 334 days.

(21) Appl. No.: 13/811,488

(22) PCT Filed: Jul. 20, 2011

(86) PCT No.: PCT/EP2011/062467
§ 371 (c)(1),
(2), (4) Date: Mar. 20, 2013

(87) PCT Pub. No.: WO2012/010640
PCT Pub. Date: Jan. 26, 2012

(65) Prior Publication Data
US 2013/0213688 A1    Aug. 22, 2013

(30) Foreign Application Priority Data

Jul. 22, 2010 (EP) .................................... 10170479

(51) Int. Cl.
| | | |
|---|---|---|
| *H01B 7/00* | (2006.01) | |
| *C08F 236/04* | (2006.01) | |
| *H01B 3/00* | (2006.01) | |
| *C07C 409/18* | (2006.01) | |
| *C08F 210/02* | (2006.01) | |
| *H01B 3/30* | (2006.01) | |
| *C08F 210/16* | (2006.01) | |

(52) U.S. Cl.
CPC ........... *C08F 236/045* (2013.01); *C07C 409/18* (2013.01); *C08F 210/02* (2013.01); *H01B 3/00* (2013.01); *H01B 3/30* (2013.01); *C07C 2101/08* (2013.01); *C07C 2101/14* (2013.01); *C08F 210/16* (2013.01)

(58) Field of Classification Search
USPC ........................................... 174/110 R–120 R
See application file for complete search history.

(56) References Cited

U.S. PATENT DOCUMENTS

| | | | |
|---|---|---|---|
| 2,528,523 A | 11/1950 | Kent | |
| 2,601,224 A | 6/1952 | Roedel | |
| 2,670,384 A | 2/1954 | Miles | |
| 3,079,370 A | 2/1963 | Precopio et al. | |
| 3,082,236 A * | 3/1963 | Mageli et al. | ................. 558/263 |
| 3,738,866 A | 6/1973 | Martens | |
| 3,755,369 A | 8/1973 | Yun | |
| 4,289,914 A * | 9/1981 | McKellin | ........................ 568/567 |
| 4,617,324 A * | 10/1986 | Muenchow et al. | ............. 521/96 |
| 5,153,272 A | 10/1992 | Chiodini et al. | |
| 5,157,087 A * | 10/1992 | Hogt et al. | ..................... 525/298 |
| 5,276,202 A * | 1/1994 | Ceh et al. | ....................... 568/559 |
| 6,225,510 B1 | 5/2001 | Frenkel et al. | |

FOREIGN PATENT DOCUMENTS

| | | | | |
|---|---|---|---|---|
| DE | 63491 A | 9/1968 | | |
| DE | WO 2009/007116 A1 * | 1/2009 | ............... H01B 3/44 |
| DE | WO 2009/007119 A2 * | 1/2009 | ............... H01B 3/44 |
| EP | 0273990 | 7/1988 | | |
| EP | 0579434 A1 | 1/1994 | | |
| EP | 1304705 | 4/2003 | | |
| GB | 1044397 | 9/1966 | | |
| GB | 1131825 A | 10/1968 | | |
| GB | 1294154 A | 10/1972 | | |
| GB | 1588870 A | 4/1981 | | |
| JP | 03006246 | 1/1991 | | |
| JP | EP 0579434 A1 * | 1/1994 | ............ C07C 409/16 |
| JP | 11213772 | 8/1999 | | |
| JP | 200529605 | 2/2005 | | |
| WO | WO96/03444 A1 | 2/1996 | | |
| WO | WO2009/007116 A1 | 1/2009 | | |
| WO | WO2009/007117 A1 | 1/2009 | | |
| WO | WO2009/007118 A1 | 1/2009 | | |
| WO | WO2009/007119 A2 | 1/2009 | | |

OTHER PUBLICATIONS

International Search Report and Written Opinion for Application No. PCT/EP2011/062467 dated Oct. 21, 2011.
Kochi et al., Chemistry of Alkoxy Radicals: Cleavage Reactions, Cleavage of Alkoxy Radicals, 84:1193:1197 (Apr. 5, 1962).
Milas et al., The Synthesis and Thermal Decomposition of Di-triethylmethyl, t-Butyl Pentannethylethyl and t-Butyl 1-Methylcyclohexyl-1-Peroxides, Synthesis and Thermal Decomposition of Complex Peroxides, 68:1939-1940 (1946).
Petrovskaya, et al., Russian Journal of Organic Chemistry, vol. 20, No. 6, 1984, pp. 1148-1151.
Supichenko, G.N., et al., Photoconversions of Acetylene Diperoxides in a Liquid Phase, Kinetics and Catalysts, vol. 38, No. 2, 1997, pp. 215-219.
Yuvchenko, A.P., et al., "Thermal Stability of Peroxyalkynes," Russian Journal of General Chemnistry, vol. 74, No. 7, 2004, pp. 1031-1037.

* cited by examiner

*Primary Examiner* — William H Mayo, III
(74) *Attorney, Agent, or Firm* — Meunier Carlin & Curfman LLC

(57) ABSTRACT

Compounds for use as radical generating agents for modifying polymer compositions, wherein the modified polymer compositions and the process for preparing the polymer compositions are utilized with wires or cables thereby forming one or more layers of a wire of the cable.

15 Claims, No Drawings

MODIFIED POLYMER COMPOSITIONS, MODIFICATION PROCESS AND FREE RADICAL GENERATING AGENTS FOR I.A. WIRE AND CABLE APPLICATIONS

FIELD OF INVENTION

The invention relates to a process for modifying a polymer composition, to modified polymer compositions, to an article, preferably wire or cable, comprising said modified polymer composition, to a process for preparing an article, preferably a wire or cable, to the use of said modified polymer in one or more layers of a wire or cable, as well as to a compound for use as a radical generating agent for modifying a polymer composition.

BACKGROUND ART

It is known to use free radical generating agents for modifying a product, such as a polymer composition via a radical reaction.

Free radical agents are used e.g. to initiate (a) crosslinking in a polymer, i.a. primarily formation of interpolymer crosslinks (bridges) by radical reaction, (b) grafting in a polymer, i.e. introduction of compounds to a polymer chain (to backbone and/or side chains) by radical reaction, and (c) visbreaking in a polymer, i.e. modification of melt flow rate (MFR) of a polymer by radical reaction. These polymer modifications are well known in the art.

When added to a polymer composition, free radical generating agents act by generating radicals, typically by decomposing to radicals, under conditions which enable the radical formation. The decomposed radicals initiate further radical reactions within a polymer composition. The resulting decomposition products of the free radical generating agent are typically a result of several reactions of the decomposition products of the initial radical forming reaction. Said resulting decomposition products typically remain in the modified polymer and may include detrimental, undesired decomposition products.

Peroxides are very common free radical generating agents used i.a. in the polymer industry for said polymer modifications. The resulting decomposition products of peroxides may include volatile by-products. For example, dicumylperoxide, which is commonly used peroxide in polymer field, decomposes i.a. to methane, acetophenone and cumylalcohol during the radical formation step, e.g. during a crosslinking step. The formed gaseous methane ($CH_4$) is flammable, explosive and volatile and thus a risk in a working environment.

In wire and cable applications, a typical cable comprises at least one conductor surrounded by one or more layers of polymeric materials. In some power cables, including medium voltage (MV), high voltage (HV) and extra high voltage (EHV) cables, said conductor is surrounded by several layers including an inner semiconductive layer, an insulation layer and an outer semiconductive layer, in that order. The cables are commonly produced by extruding the layers on a conductor. One or more of said layers are then typically crosslinked to improve i.a. deformation resistance at elevated temperatures, as well as mechanical strength and/or chemical resistance, of the layer(s) of the cable. The free radical generating agent, such as peroxide, is typically incorporated into the layer material prior to the extrusion of the layer(s) on a conductor. After formation of the layered cable, the cable is then subjected to a crosslinking step to initiate the radical formation and thereby crosslinking reaction.

The decomposition products of the free radical forming agent remain mostly captured within the cable layer after crosslinking. This causes problems in view of the cable manufacturing process as well as in view of the quality of the final cable.

Accordingly, after crosslinking the cable must be cooled with great care to prevent the gaseous volatile decomposition products like methane forming voids within the polymer layer. These voids have typically an average diameter of between 10 to 100 µm. Partial discharges can take place in such voids within a cable that is subjected to an electrical field and thereby reduce the electrical strength of the cable.

The MV, HV and EHV power cables must have high layer quality in terms of safety during installation and in end use thereof. In service, volatile decomposition products in a cable resulting from a crosslinking step can create a gas pressure and thus cause defects in the shielding and in the joints. E.g. when a cable is equipped with a metal barrier, then the gaseous products can exert a pressure, especially on the joints and terminations, whereby a system failure may occur.

For the above reasons the volatile decomposition products, such as methane e.g. where dicumylperoxide is used, are conventionally reduced to a minimum or removed after crosslinking and cooling step. Such a removal step is generally known as a degassing step.

The degassing step is time and energy consuming and is thus a costly operation in a cable manufacturing process. Degassing requires large heated chambers which must be well ventilated to avoid the build-up of e.g. flammable methane and ethane. The cable, typically wound to cable drums, is normally degassed at elevated temperature in the range of 50-80° C., e.g. 60-70° C., for lengthy time periods. At these temperatures however, thermal expansion and softening of the insulation can occur and lead to undue deformation of the formed cable layers resulting directly in failures of the cable. The degassing of MV, HV and EHV cables with high cable weight needs thus often to be carried out at decreased temperatures.

Accordingly, there is a need to find new solutions to overcome the prior art problems.

DESCRIPTION OF THE INVENTION

The objects of the invention are solved by the compounds, polymer compositions, end products and processes as defined inter alia (i.a.). in the description and claims below.

COMPOUNDS OF THE INVENTION

Accordingly, in a first embodiment, the invention provides a compound of formula (I)

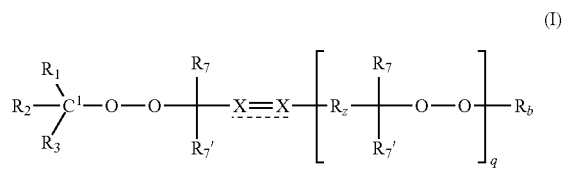

(I)

wherein q=0-5;
each X is CH, C or N provided that at least one X is C or CH;
the dotted line is an optionally present bond (i.e. when both X groups are C);

Rz is a covalent bond or a divalent group —Ry-X═X— or —Ry-C≡C—; provided that at least one X is CH;

Ry is divalent substituted or unsubstituted saturated or partially unsaturated hydrocarbyl or substituted or unsubstituted aromatic hydrocarbyl group;

wherein said substituted or unsubstituted saturated or partially unsaturated hydrocarbyl or aromatic hydrocarbyl optionally comprises 1 to 6 heteroatoms;

wherein said substituted saturated or partially unsaturated hydrocarbyl or substituted aromatic hydrocarbyl comprise independently 1 to 8 substituents selected from a functional group, a saturated or partially unsaturated hydrocarbyl optionally bearing a functional group, a saturated or partially unsaturated hydrocarbyl optionally interrupted by 1 to 4 heteroatoms or aromatic hydrocarbyl optionally bearing a functional group;

$R_7$ and $R_{7'}$ can be the same or different and are independently selected from an unsubstituted saturated or unsubstituted partially unsaturated hydrocarbyl group;

Rb is H or is the group $C^{1'}(R_{1'}R_{2'}R_{3'})$;

$R_1$ and $R_{1'}$ are each independently H, substituted or unsubstituted saturated or partially unsaturated hydrocarbyl or substituted or unsubstituted aromatic hydrocarbyl;

wherein each of said substituted or unsubstituted saturated or partially unsaturated hydrocarbyl or aromatic hydrocarbyl optionally comprises 1 to 6 heteroatoms;

wherein said substituted saturated or partially unsaturated hydrocarbyl or substituted aromatic hydrocarbyl comprise independently 1 to 4 substituents selected from a functional group, a saturated or partially unsaturated hydrocarbyl optionally bearing a functional group or aromatic hydrocarbyl optionally bearing a functional group;

$R_2$, $R_{2'}$, $R_3$ and $R_{3'}$ are each independently H, substituted or unsubstituted saturated or partially unsaturated hydrocarbyl or substituted or unsubstituted aromatic hydrocarbyl;

wherein each of said substituted or unsubstituted saturated or partially unsaturated hydrocarbyl or aromatic hydrocarbyl optionally comprises 1 to 6 heteroatoms;

wherein said substituted saturated or partially unsaturated hydrocarbyl or substituted aromatic hydrocarbyl optionally comprise independently 1 to 4 substituents selected from a functional group or a saturated or partially unsaturated hydrocarbyl optionally bearing a functional group or aromatic hydrocarbyl optionally bearing a functional group; or $R_2$ and $R_3$ together with the carbon atom ($C^1$) to which they are attached form an unsubstituted or substituted saturated or partially unsaturated carbocyclic ring moiety of 3 to 14 C-atoms, preferably 5 to 12-C atoms; an unsubstituted or substituted saturated or partially unsaturated heteroring moiety of 3 to 14 ring atoms comprising 1 to 6, preferably 1 to 4 heteroatoms, selected from O, N, P, S or Si; or an unsubstituted or substituted aromatic ring moiety of 3 to 14 C-atoms, preferably of 5 to 12 C-atoms, optionally comprising 1 to 4 heteroatoms;

wherein said substituted carbocyclic ring, heteroring or aromatic ring system comprises 1 to 4 substituents selected independently from a functional group, or a saturated or partially unsaturated hydrocarbyl optionally bearing a functional group, or aromatic hydrocarbyl optionally bearing a functional group; or $R_{2'}$ and $R_{3'}$ together with the carbon atom ($C^{1'}$) to which they are attached form an unsubstituted or substituted saturated or partially unsaturated carbocyclic ring moiety of 3 to 14 C-atoms, preferably of 5-12 C atoms; an unsubstituted or substituted saturated or partially unsaturated heteroring moiety of 3 to 14 ring atoms comprising 1 to 6, preferably 1 to 4 heteroatoms, selected from O, N, P, S or Si; or unsubstituted or substituted aromatic ring moiety of 3 to 14 C-atoms, preferably moiety of 5 to 12 C-atoms; optionally comprising 1 to 4 heteroatoms;

wherein said substituted carbocyclic ring, heteroring or aromatic ring system comprises 1 to 4 substituents selected independently from a functional group or a saturated or partially unsaturated hydrocarbyl optionally bearing a functional group or aromatic hydrocarbyl optionally bearing a functional group;

with a proviso that at least two of $R_1$, $R_2$ and $R_3$ are other than H or methyl;

or that at least one of $R_1$, $R_2$ and $R_3$ is an alkenyl or alkynyl group;

or a functional derivative thereof.

Where q is 0 then the compound of the invention is of formula (II)

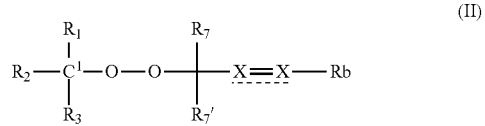

(II)

wherein $R_1$, $R_2$, $R_3$, Rb, $R_7$, $R_{7'}$, and X are as hereinbefore defined.

The subscript q is, however, preferably 1-3, more preferably 1 or 2, most preferably 1.

A preferable subgroup of the compounds of formula (I) of the invention is therefore compounds of formula (III) (where q is 1 and Rb is $C^{1'}(R_{1'}R_{2'}R_{3'})$;

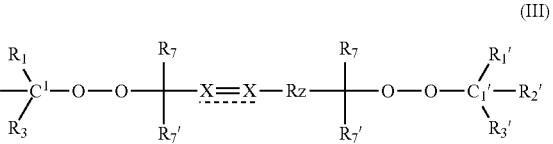

(III)

wherein $R_{1-3}$, $R_{1'}$-$R_{3'}$; $R_7$, $R_{7'}$, X and Rz are as defined in formula (I).

The compounds of formula (I) of the invention and any subgroups thereof are also referred to herein as compounds of the invention or compounds (I).

It has unexpectedly found that the compound (I) forms reduced or no detectable amounts of decomposition products that can be undesired in many demanding end applications, such as in wire and cable applications.

Without limiting to any theory, the terms "a decomposition product(s) thereof" or "a decomposition product of a free radical generating step" etc. as used above and below mean herein a by-product(s) formed during a free radical generating step, e.g. crosslinking step, and possibly also during the cooling step, by initiation of the free radical generating agent, as well known in the art. As an example methane may be one decomposition product which is an undesired decomposition product of the invention. Further decomposition products are specified below, which may not be desired in various embodiments of the invention.

The term "a free radical generating agent" is defined herein above or below to be any compound capable of generating radicals, e.g. in industrial applications, e.g. which can initiate a modification reaction in a polymer, such as a crosslinking, grafting or visbreaking reaction in a polymer and therefore refers to the peroxides of the invention.

The compounds of the invention when used as a free radical generating agent can preferably result in methane ($CH_4$) content of less than 200 ppm (weight), preferably of less than 100 ppm (weight), as a decomposition product thereof, when determined according to the GC-Analysis protocol as described under "Determination methods".

Generally, in above and below definitions the given values in ppm for methane and/or other volatile content are determined by gas chromatography from the obtained crosslinked polymer composition as such or from a crosslinked cable layer, depending on the definition, according to a method as described below under "GC-analysis protocol". Accordingly, the produced methane or other volatile content can equally be determined from a crosslinked polymer composition as such or from a crosslinked manufactured article thereof, as desired, each consisting of the polymer composition of the invention. The sample under the test is crosslinked using the test free radical generating agent in such an amount which results in a crosslinking degree expressed as gel content of at least 50%. The gel content (%) is measured according to ASTM D2765-01 Method A or B (depending on the nature of the sample). Such a crosslinked sample is then used for preparing the sample for volatile content measurement of GC-analysis protocol.

In one embodiment said compound of the invention results in reduced amount of, e.g. less than 200 ppm, low molecular weight compounds selected from (C1-C3)alkanes (measured analogously to "GC-analysis protocol" below) when generating free radicals, e.g. in industrial applications.

In another embodiment of the invention it is advantageous that said compound as a free radical generating agent results in reduced amount of, e.g. less than 200 ppm, (C1-C4)alkanes (measured analogously to "GC-analysis protocol" below) as decomposition products thereof when generating free radicals, e.g. in industrial applications.

In embodiments, wherein very high quality is required for the products modified by using a free radical agent, then it is preferable that said compound results in reduced amount of, e.g. less than 200 ppm, (C1-C6)alkanes (measured analogously to "GC-analysis protocol" below) as decomposition products thereof during a free radical forming step, e.g. in an industrial process.

Without limiting to any theory, the moiety O—O—C($R_7R_{7'}$)X=X or O—O—C($R_7R_{7'}$)C≡C group is believed to play a role in the advantageous properties of the compounds of the invention, in particular in terms of the reduced amounts of volatile by-products produced during their decomposition, in particular reduced amounts of methane. Accordingly, where there are two or more peroxide (O—O) groups in a compound of the invention, it is preferred that one of the oxygen atoms of O—O group is linked to a —C($R_7R_{7'}$)X=X or —C($R_7R_{7'}$)C≡C group (such that the O group bonds to the C($R_7R_{7'}$) group. Also the $C^1(R_1R_2R_3)$ moiety is believed to contribute to the beneficial low amount of decomposition products.

DEFINITIONS

When the substituents are defined herein as "hydrocarbyl", "aromatic hydrocarbyl", "alkyl" etc. it is evident that they mean "a hydrocarbyl group", "an alkyl group" etc. The substituents are referred herein interchangeably as "radical" or "group", as known in the field.

The term unsaturated bond is used here to refer to a double bond or triple bond but does not cover an aromatic link as in a phenyl ring.

A hydrocarbyl group can be linear, branched or cyclic or a mixture of cyclic and linear or branched groups. For the avoidance of doubt, the term "hydrocarbyl" used herein does not encompass aromatic groups as is clear from the definitions used herein.

Any hydrocarbyl group of the invention will preferably have up to 40 C-atoms, preferably up to 30 C-atoms, e.g. up to 20-C atoms, especially up to 12 carbon atoms. Some highly preferred hydrocarbyls may have 1 to 6 carbon atoms. The term hydrocarbyl is not intended to cover aromatic groups as these are defined separately herein.

Alkyl groups, alkenyl groups or alkynyl groups will preferably have up to 40 C-atoms, preferably up to 30 C-atoms, e.g. up to 20-C atoms. Some highly preferred alkyl groups may have 1 to 12 carbon atoms, more preferably may be methyl or have 2 to 12 carbon atoms, e.g. 6 to 12 carbon atoms. Such groups can be linear or branched.

Cyclic alkyl or cyclic alkenyl groups will preferably have up to 20 C atoms, especially up to 12 carbon atoms. Some highly preferred cyclic alkyl groups may have 3 to 8 carbon atoms. Preferred cyclic alkenyl groups may have 5 to 8 carbon atoms. Cyclic hydrocarbyl groups may carry linear or branched hydrocarbyl side chains (e.g. alkyl or alkenyl side chains).

Aromatic hydrocarbyl groups may have up to 40 C-atoms, preferably up to 30 C-atoms, e.g. up to 20 C-atoms, especially up to 12 carbon atoms. Some highly preferred aromatic hydrocarbyls may have 6 to 12 carbon atoms.

The expression "partially unsaturated" means that the moiety may comprise one or more double or triple bonds and includes alkenyl radicals comprising at least one double bond and alkynyl radicals comprising at least one triple bond. In case of "partially unsaturated cyclic hydrocarbyl" there can be one or more double bonds in the ring systems meaning that the ring is non-aromatic to differentiate said "partially unsaturated" ring moieties from "aromatic rings" such as phenyl or pyridyl radicals.

"Hetero atoms" present in the moieties of the invention are selected from N, O, P, S or Si, preferably O, P, S or N, especially O, S or N, most especially O or N. It will be appreciated that where e.g. an N atom is present, this will need an H atom or other substituent to fulfill its valency.

The expression "monocyclic" includes monocyclic ring systems, such as cyclopentyl, cyclohexyl, cycloheptyl or phenyl.

The expression "multicyclic" means herein fused ring systems, such as naphthyl.

Unless otherwise defined herein, the term "carbocyclic" means substituted or unsubstituted saturated or partially unsaturated cyclic hydrocarbyl ring system; or substituted or unsubstituted aromatic hydrocarbyl ring system.

The term "functional group" as a substituent is a well known expression for a pendant substituent having a chemically functional group and includes i.a. —OH, —$NR_2$, wherein each R is independently H or (C1-C12)alkyl; —OR", wherein R" is i.a. H, (C1-C12)alkyl or —$NR_2$, wherein each R is as defined for —$NR_2$; nitro; —SH; —S($C_{1-12}$)alkyl; —CN; —COR", —COOR", wherein R" is as defined for —OR"; or halogen, such as —F, —Cl, Br or —I. Preferably the functional group is —OH, —$NR_2$, —OR" or halogen.

The term "optional" means "may or may not be present", e.g. "optionally substituted" covers the possibilities that a substituent is present or is not present. The term "unsubstituted" naturally means that no substituent is present.

In compounds of the invention where $R_2$ and $R_3$ groups form together with $C^1$ an aromatic ring as defined above, then $R_1$ is not present, and, respectively, when $R_{2'}$ and $R_{3'}$ groups form together with $C^{1'}$ an aromatic ring, as defined above, then a $R_{1'}$ is not present. Preferably however $R_2$ and $R_3$ together with $C^1$ and $R_{2'}$ and $R_{3'}$ together with $C^{1'}$ do not form an aromatic ring.

By "functional derivative" of the compounds of the invention means that at least one of $R_1$, $R_2$, $R_3$, $R_{1'}$, $R_{2'}$, $R_{3'}$ is in form of functional derivative. The term "functional derivative" includes i.a. esters and salts of compounds of the invention, in particular esters and salts of substituents $R_1$, $R_2$, $R_3$, $R_{1'}$, $R_{2'}$, $R_{3'}$. Preferred compounds (I) are those, wherein $R_1$, $R_2$, $R_3$, $R_{1'}$, $R_{2'}$, $R_{3'}$ are as defined above or below are not functional derivatives thereof.

DETAILED DESCRIPTION OF THE COMPOUNDS OF THE INVENTION

Preferred aspects discussed above and below with respect to formula (I) also apply to all compounds of the invention.

The following subgroups of the compound of formula (I) of the invention represent some preferable embodiments and variants of the invention. It is also understood that said below subgroups further specify the substituents given above in formula (I). Each subgroups definition can be combined with any other subgroup as defined above or below to define further preferred subgroups within the broadest scope of compounds of the invention.

Moreover said above generally defined compounds and said subgroups thereof, and the general definition for compounds of the invention, as well as said subgroups thereof, above or below, can be combined in any combination in their uses for modifying polymers, to modification methods, to modified polymers and to articles comprising said modified polymers, as well as to preparation process thereof, which all aspects of the invention are discussed below.

In any compound of the invention, at least one X atom is a carbon atom. It is preferred if both X atoms are the same and hence are preferably both carbon atoms. Where multiple X atoms are present these are all preferably the same. It will be appreciated that where one X is N then there cannot be a triple bond present and only a double bond can be used when X is N. Most preferably, all X atoms are carbon atoms. The preferred X=X or X≡X groups are therefore —CH=CH— or —C≡C—.

In all formulae of the invention it is preferred if the $R_7$ and $R_{7'}$ groups attached to the same carbon atom are the same. Where the compound of the invention comprises more than two $C(R_7R_{7'})$ units, it is preferred if these are all the same. Preferably $R_7$ and $R_{7'}$ groups are alkyl, more preferably $C_{1-6}$-alkyl, most preferably methyl. Preferably all $R_7$ and $R_{7'}$ groups are methyl.

As noted above, the subscript q is preferably 1-3, more preferably 1 or 2, most preferably 1 (e.g. forming a compound of formula (III)).

Rz preferably represents a covalent bond. This means that the most preferred linking group from the $C(R_7R_{7'})$ group to Rb or between $C(R_7R_{7'})$ groups is a double bond or triple bond, in particular a carbon carbon double bond or carbon carbon triple bond. Preferably the linker is a carbon carbon triple bond.

If present, Ry represents a divalent substituted or unsubstituted saturated or partially unsaturated hydrocarbyl or substituted or unsubstituted aromatic hydrocarbyl;

wherein said substituted or unsubstituted saturated or partially unsaturated hydrocarbyl or aromatic hydrocarbyl optionally comprises 1 to 6 heteroatoms;

wherein said substituted or unsubstituted saturated or partially unsaturated hydrocarbyl or substituted aromatic hydrocarbyl comprise independently 1 to 8 substituents selected from a functional group, a saturated or partially unsaturated hydrocarbyl optionally bearing a functional group, a saturated or partially unsaturated hydrocarbyl optionally interrupted by 1 to 4 heteroatoms or aromatic hydrocarbyl optionally bearing a functional group.

Accordingly, in one embodiment of formula (I) (and (III)), the group linking the $CR_7R_{7'}$ unit may therefore represent a —C=C-Ry-C=C— group, —C=C-Ry-C≡C— group, a —C≡C-Ry-C=C— group or —C≡C-Ry-C≡C— group.

The Ry group therefore forms a divalent linker between groups in question and may also have side groups as defined above. The Ry group preferably comprises an unsubstituted or substituted saturated or partially unsaturated hydrocarbyl group. Preferably, the use of an aromatic group is avoided for Ry.

It is within the scope of the invention for the Ry group to be substituted by 1 to 8 substituents selected independently from functional group above or below or a saturated or partially unsaturated hydrocarbyl optionally bearing a functional group, a saturated or partially unsaturated hydrocarbyl optionally interrupted by 1 to 4 heteroatom(s) or aromatic hydrocarbyl optionally bearing a functional group, above or below.

In a further embodiment, the Ry group can be interrupted by 1 to 6 heteroatoms, especially 1 to 6 O, S, N or P atoms, e.g. 1 to 6 O, S or N atoms. Preferably, there will be 0 to 4, more preferably 0 to 3, especially 0 to 2 such heteroatoms in the Ry group.

In one embodiment Ry is a divalent hydrocarbyl, preferably (C1-C6) alkylene, substituted by O—O—$C(R_1R_2R_{3'})$ or $C(R_7R_{7'})$—O—O—$C(R_1R_2R_{3'})$. Thus in this embodiment a dentrimeric type structure is formed.

Where $R_y$ is present, it is most preferably linear or branched C1-10 alkylene group, more preferably C1-C6 alkylene, especially a linear C1-C6 alkylene. If branched, then there may be 1 to 4, preferably 1 to 2, branches, such as methyl. Especially preferred Ry groups are $CH_2$, $CH_2CH_2$, and —$(CH_2)_3$—

The Rz group is most preferably a covalent bond however, and hence there is preferably no Ry group in the compounds of the invention.

$R_1$ and $R_{1'}$ are each independently H, substituted or unsubstituted saturated or partially unsaturated hydrocarbyl or substituted or unsubstituted aromatic hydrocarbyl;

wherein each of said substituted or unsubstituted saturated or partially unsaturated hydrocarbyl or aromatic hydrocarbyl optionally comprises 1 to 6 heteroatoms;

wherein said substituted or unsubstituted saturated or partially unsaturated hydrocarbyl include, preferably is selected from, (i) straight or branched chain saturated or partially unsaturated hydrocarbyls, (ii) straight or branched chain saturated or partially unsaturated hydrocarbyls which bear saturated or partially unsaturated cyclic hydrocarbyl and (iii) saturated or partially unsaturated cyclic hydrocarbyls;

wherein each of said aromatic hydrocarbyl and said saturated or partially unsaturated cyclic hydrocarbyl is independently a monocyclic or multicyclic ring system; and wherein said substituted saturated or partially unsaturated hydrocarbyl or substituted aromatic hydrocarbyl comprise independently 1 to 4 substituents selected from a functional group, a saturated or partially unsaturated hydrocarbyl optionally bearing a functional group or aromatic hydrocarbyl optionally bearing a functional group;

$R_2$, $R_{2'}$, $R_3$ and $R_{3'}$ are each independently H, substituted or unsubstituted saturated or partially unsaturated hydrocarbyl or substituted or unsubstituted aromatic hydrocarbyl;

wherein each of said substituted or unsubstituted saturated or partially unsaturated hydrocarbyl or aromatic hydrocarbyl optionally comprises 1 to 6 heteroatoms;

wherein said substituted or unsubstituted saturated or partially unsaturated hydrocarbyl include (i) straight or branched chain saturated or partially unsaturated hydrocarbyls, (ii) straight or branched chain saturated or partially unsaturated hydrocarbyls which bear saturated or partially unsaturated cyclic hydrocarbyl and (iii) saturated or partially unsaturated cyclic hydrocarbyls;

wherein each of said aromatic hydrocarbyl and said saturated or partially unsaturated cyclic hydrocarbyl is independently a monocyclic or multicyclic ring system; and wherein said substituted saturated or partially unsaturated hydrocarbyl or substituted aromatic hydrocarbyl comprise independently 1 to 4 substituents selected from a functional group or a saturated or partially unsaturated hydrocarbyl optionally bearing a functional group or aromatic hydrocarbyl optionally bearing a functional group; or $R_2$ and $R_3$ together with the carbon atom ($C^1$) to which they are attached form an unsubstituted or substituted saturated or partially unsaturated carbocyclic ring moiety of 3 to 14 C-atoms, preferably 5 to 12 C-atoms; an unsubstituted or substituted saturated or partially unsaturated heteroring moiety of 3 to 14 ring atoms comprising 1 to 6, preferably 1 to 4 heteroatoms, selected from O, N, P, S or Si; or an unsubstituted or substituted aromatic ring moiety of 3 to 14 C-atoms, preferably of 5-12 C atoms, optionally comprising 1 to 4 heteroatoms;

wherein said carbocyclic ring, heteroring or aromatic ring system is optionally fused with another optionally substituted ring system having 4 to 14 ring atoms; and wherein said substituted carbocyclic ring, heteroring or aromatic ring system comprises 1 to 4 substituents selected independently from a functional group, or a saturated or partially unsaturated hydrocarbyl optionally bearing a functional group, or aromatic hydrocarbyl optionally bearing a functional group; or $R_{2'}$ and $R_{3'}$ together with the carbon atom ($C^{1'}$) to which they are attached form an unsubstituted or substituted saturated or partially unsaturated carbocyclic ring moiety of 3 to 14 C-atoms, preferably of 5 to 12 C-atoms; an unsubstituted or substituted saturated or partially unsaturated heteroring moiety of 3 to 14 ring atoms comprising 1 to 6, preferably 1 to 4 heteroatoms, selected from O, N, P, S or Si; or unsubstituted or substituted aromatic ring moiety of 3 to 14 C-atoms, preferably moiety of 5 to 12 C-atoms; optionally comprising 1 to 4 heteroatoms;

wherein said carbocyclic ring, heteroring or aromatic ring system is optionally fused with another optionally substituted ring system having 4 to 14 ring atoms; and wherein said substituted carbocyclic ring, heteroring or aromatic ring system comprises 1 to 4 substituents selected independently from a functional group or a saturated or partially unsaturated hydrocarbyl optionally bearing a functional group or aromatic hydrocarbyl optionally bearing a functional group;

with a proviso that at least two of $R_1$, $R_2$ and $R_3$, are other than H or methyl;

or that at least one of $R_1$, $R_2$ and $R_3$ is an alkenyl or alkynyl group; or a functional derivative thereof.

Preferred Options of $R_1$ to $R_3$ and $R_{1'}$ to $R_{3'}$ (Relevant to all Compounds of the Invention)

It is preferred if at least two of $R_1$, $R_2$ and $R_3$, and at least two of $R_{1'}$, $R_{2'}$ and $R_{3'}$, respectively, are other than H or methyl. It is also preferred if none of $R_1$, $R_2$ and $R_3$, and none of $R_{1'}$, $R_{2'}$ and $R_{3'}$ are H.

The substituents $R_1$, $R_2$, $R_3$, $R_{1'}$, $R_{2'}$ and $R_{3'}$ of compounds of the invention may each independently optionally carry 1 to 4 substituents as defined above. Said optional substituents may preferably be selected each independently from a functional group as defined above; saturated or partially unsaturated hydrocarbyl optionally bearing a functional group; or aromatic hydrocarbyl optionally bearing a functional group, as defined above. Preferably the substituent is a C1-12 hydrocarbyl (e.g. C1-6 alkyl) or from a functional groups as defined above. If a substituent is present, preferably 1 substituent is present. Ideally $R_1$, $R_2$, $R_3$, $R_{1'}$, $R_{2'}$ and $R_{3'}$ are not substituted.

In a preferred embodiment of the invention the group formed by $R_1$-$R_3$ and $C^1$ and the group formed by $R_{1'}$-$R_{3'}$ and $C^{1'}$ are identical. The compounds of the invention are preferably symmetrical.

Embodiment A

A first preferable embodiment (A) comprises a subgroup (1) of the compound of formula (I) as defined above, wherein $R_2$ and $R_3$ together with carbon atom ($C^1$) to which they are attached form an optionally substituted carbocyclic ring moiety of 3 to 14 ring C-atoms or an optionally substituted heteroring moiety of 3 to 14 ring atoms containing 1 to 6, preferably 1 to 4, heteroatoms selected from O, N, P or S. Such a ring moiety may be monocyclic or multicyclic, preferably monocyclic.

Carbocyclic rings are preferably non aromatic, especially saturated rings. Heterorings are preferably non aromatic, especially saturated rings.

Preferably $R_2$ and $R_3$ together with carbon atom ($C^1$) form a (C3-C14) carbocyclic ring moiety. The (C3-C14) carbocyclic ring moiety may optionally be substituted with 1 to 4 substituents which are preferably selected from substituents (Z) as defined later below.

In a subgroup (2) of the compound of formula (I) as defined above, $R_{2'}$ and $R_{3'}$ together with carbon atom ($C^{1'}$) to which they are attached form an optionally substituted carbocyclic ring moiety of 3 to 14 ring C-atoms or an optionally substituted heteroring moiety of 3 to 14 ring atoms containing 1 to 6, preferably 1 to 4, heteroatoms selected from O, N, P, or S. Such a ring moiety may be monocyclic or multicyclic, preferably monocyclic.

Preferably $R_{2'}$ and $R_{3'}$ together with carbon atom ($C^{1'}$) form a (C3-C14) carbocyclic ring moiety. Said (C3-C14) carbocyclic ring moiety may optionally be substituted with 1 to 4 substituents which are preferably selected from substituents (Z) as defined later below.

In a subgroup (3) of the compound of formula (I) as defined above, $R_2$ and $R_3$ together with the carbon atom ($C^1$) to which they are attached form an optionally substituted, saturated or partially unsaturated mono- or bicyclic (C4-C14) carbocyclic ring, preferably unsubstituted saturated monocyclic (C5-C8) carbocyclic ring, such as cyclopentyl, cyclohexyl or cycloheptyl, preferably cyclohexyl or cyclopentyl. Also preferably, in said subgroup (3), $R_2$ and $R_3$ together with the carbon atom ($C^1$) to which they are attached may form a saturated monocyclic (C5-C8) carbocyclic ring, such as cyclopentyl, cyclohexyl or cylcoheptyl, preferably cyclohexyl or cyclopentyl, which is substituted with 1 to 4 substituents which are preferably selected from substituents (Z) as defined later below.

In a subgroup (4) of the compound of formula (I) as defined above, $R_{2'}$ and $R_{3'}$ together with the carbon atom ($C^{1'}$) to which they are attached form an optionally substituted, saturated or partially unsaturated mono- or bicyclic (C4-C14) carbocyclic ring, preferably unsubstituted saturated monocyclic (C5-C8) carbocyclic ring, such as cyclopentyl, cyclohexyl or cylcoheptyl, preferably cyclohexyl or cyclopentyl. Also preferably in said subgroup (4) $R_{2'}$ and $R_{3'}$ together with the carbon atom ($C^{1'}$) they are attached to may form a saturated monocyclic (C5-C8) carbocyclic ring, such as cyclopentyl, cyclohexyl or cylcoheptyl, preferably cyclohexyl or cyclopentyl, which is substituted with 1 to 4 substituents which are preferably selected from substituents (Z) as defined later below, e.g. one substituent Z.

More preferably, in a subgroup (5a) of the compounds (I), $R_2$ and $R_3$ and, respectively, $R_{2'}$ and $R_{3'}$ form carbocyclic rings as defined in formula (I), more preferably form carbocyclic rings as defined in subgroups (1) and, respectively, (2), even more preferably form carbocyclic rings as defined in subgroups (3) and, respectively, (4), which may be substituted with 1 to 4 substituents which are preferably selected from substituents (Z) as defined later below, e.g. one substituent Z.

In an even preferable subgroup (5b) of the compound of formula (I) as defined above, $R_2$ and $R_3$ together with the carbon atom ($C^1$) to which they are attached form a ring system as defined in subgroup (3) and $R_{2'}$ and $R_{3'}$ together with the carbon atom ($C^{1'}$) to which they are attached form a ring system as defined in subgroup (4), whereby the ring system formed by $R_{2'}$ and $R_{3'}$ together with the carbon atom ($C^{1'}$) is identical to the ring system formed by $R_2$ and $R_3$ together with the carbon atom ($C^1$).

Subgroups 1 to 5b form part of embodiment (A) of the invention, i.e. where the substituents $R_1$ and $R_{1'}$ are as defined in formula (I) above. These subgroups can be combined with any $R_1$ and $R_{1'}$ substituent.

Highly preferred subgroups of embodiment (A), are the subgroup (5a) and even more preferably subgroup (5b).

Embodiment B

A second preferable embodiment (B) comprises a subgroup (6) of the compound of formula (I) as defined above, wherein $R_1, R_2, R_3, R_{1'}, R_{2'}, R_{3'}$ each independently is optionally substituted mono- or multicyclic (C5-C14)aryl; optionally substituted mono- or multicyclic (C5-C14)heteroaryl; optionally substituted mono- or multicyclic (C4-C14)cycloalkyl; optionally substituted mono- or multicyclic (C4-C14)heterocyclyl; optionally substituted straight or branched chain (C1-C50)alkyl, preferably straight chain (C1-C30) alkyl; optionally substituted straight or branched chain, preferably straight chain, (C2-C50)alkenyl, preferably straight chain (C2-C30)alkenyl; or optionally substituted straight or branched chain, preferably straight chain, (C2-C50)alkynyl, preferably straight chain (C2-C30)alkynyl; or optionally substituted straight or branched chain (C1-C50) heteroalkyl comprising 1 to 4 heteroatoms selected from N, O, S, P or Si. The optionally substituted moieties as defined above contain preferably 1 to 4 substituents which are preferably selected from substituents (Z) as defined later below.

Preferable embodiments (B) of compounds (I) are any of subgroups (7) to (11), optionally in any combinations thereof:

In a subgroup (7) of the compound of formula (I) as defined above, $R_2, R_3, R_{2'}$, and $R_{3'}$ are each independently selected from unsubstituted straight chain (C1-C50)alkyl, preferably (C1-C30)alkyl, more preferably (C1-C20)alkyl, especially C1-12 alkyl such as hexyl, heptyl, octyl, decyl, undecyl, docedyl, preferably decyl.

In a subgroup (8) of the compound of formula (I) as defined above, $R_2$ and $R_{2'}$ each represents same radical and, respectively, $R_3$ and $R_{3'}$ each represents same radical.

In a subgroup (9) of the compound of formula (I) as defined above, $R_2$ and $R_{2'}$ are same and each represents methyl or C2-10 alkenyl or C2-10 alkynyl. Where $R_{2'}$ is an C2-10 alkenyl or C2-10-alkynyl group it is also preferred if $R_1$ and $R_{3'}$ are $C_{1-6}$ alkyl groups, such as methyl groups. It is also preferred if when $R_2$ is an C2-10 alkenyl or C2-10-alkynyl group then $R_1$ and $R_3$ are $C_{1-6}$ alkyl groups, such as methyl groups.

In a subgroup (10) of the compound of formula (I) as defined above, $R_2$ and $R_{2'}$ are same and each represents (C6-C30)alkyl.

In a subgroup (11) of the compound of formula (I) as defined above, $R_3$ and $R_{3'}$ are same and each represents (C6-C30)alkyl.

Embodiment C

A third preferable embodiment (C) of the compounds (I) is a subgroup (12). In subgroup (12) of the compound of formula (I) as defined above, $R_1$ and $R_{1'}$ are same or different, preferably same, and each represents optionally substituted, saturated or partially unsaturated cyclic hydrocarbyl of 5 to 14 ring atoms optionally containing 1 to 4 heteroring atoms selected from N, O, P, S or Si, or optionally substituted mono- or multicyclic (C5-C14)aryl, preferably unsubstituted monocyclic (C5-C7)aryl. Also preferably in said subgroup (12), $R_1$ and $R_{1'}$ are same or different, preferably same and each represents substituted mono- or multicyclic (C5-C14)aryl, preferably monocyclic (C5-C7)aryl which is substituted with 1 to 4 substituents which are preferably selected from substituents (Z) as defined later below.

Embodiment D

A fourth preferable embodiment (D) of the compounds (I) is a subgroup (13). In a subgroup (13) of the compound of formula (I) as defined above, $R_1$ and $R_{1'}$ are same or different, preferably same, and each represents optionally substituted branched or straight chain, preferably unsubstituted straight chain, (C1-C30)alkyl, e.g. C1-6 alkyl, especially methyl.

For the avoidance of doubt it is stressed that the preferred definitions of $R_1$ and $R_{1'}$ given in subgroups 12 and 13 can be combined with any of the preferred substituent definitions of subgroups 1 to 11 to form even more preferred compounds.

Further preferred compounds of the invention are of subgroup (14) with the further proviso that at least two of $R_1, R_2$ and $R_3$, and at least two of $R_{1'}, R_{2'}$ and $R_{3'}$, respectively, are other than H, methyl, iso-butyl or tert-butyl.

Further preferred compounds of the invention are of subgroup (15) with the further proviso that at least two of $R_1, R_2$ and $R_3$, and at least two of $R_{1'}, R_{2'}$ and $R_{3'}$, respectively, are other than H, methyl, ethyl, 1-propyl, isopropyl, 1-butyl, isobutyl or tert-butyl.

Further preferred compounds of the invention are of subgroup (16) with the further proviso that at least two of $R_1, R_2$ and $R_3$, and at least two of $R_{1'}, R_{2'}$ and $R_{3'}$, respectively, are each other than $CH_3$ preferably other than straight or branched chain saturated or partially unsaturated (C1-C3) hydrocarbyl, more preferably other than straight or branched chain saturated or partially unsaturated (C1-C4)hydrocarbyl.

Further preferred compounds of the invention are of subgroup (17) with the further proviso that at least two of $R_1, R_2$ and $R_3$, and at least two of $R_{1'}, R_{2'}$ and $R_{3'}$, respectively, are preferably other than straight or branched chain saturated or partially unsaturated (C2-C3)hydrocarbyl, more preferably other than straight or branched chain saturated or partially unsaturated (C2-C4)hydrocarbyl.

Each of subgroups (14), (15), (16) and (17) are useful for embodiments wherein very high purity products, e.g. polymers, are desirable after the modification step with compound (I).

The preferred subgroups of the above embodiments (A), (B), (C) and (D) are the follows:

In a further preferable subgroup (Ia) of compounds (I) are selected from the embodiment (A), wherein $R_1$ and $R_{1'}$ are same or different, preferably same, and each represents optionally substituted branched or straight chain, preferably unsubstituted straight chain, (C1-C30)alkyl, which is preferably (C6-C30)alkyl; or methyl, more preferably methyl; and $R_2$ and $R_3$ together with $C^1$ atom to which they are attached form an optionally substituted, saturated or partially unsaturated mono- or bicyclic (C4-C14)carbocyclic ring, preferably optionally substituted, more preferably unsubstituted saturated monocyclic (C5-C8)carbocyclic ring;

and $R_{2'}$ and $R_{3'}$ together with the carbon atom ($C^{1'}$) to which they are attached form an optionally substituted, saturated or partially unsaturated mono- or bicyclic (C4-C14)carbocyclic ring, preferably optionally substituted, more preferably unsubstituted saturated monocyclic (C5-C8)carbocyclic ring; whereby the ring system formed by $R_2$ and $R_3$ together with $C^1$ is preferably identical to a ring system formed by $R_{2'}$ and $R_{3'}$ together with $C^{1'}$.

Any substituted moiety preferably contains 1 to 4 substituents (Z) as defined later below, e.g. one substituent Z.

Especially preferred cyclic radicals are cyclopentyl and cyclohexyl in this subgroup.

A second preferred subgroup (Ib) of compounds (I) is an embodiment (B) as defined above, wherein $R_2$, $R_{2'}$, $R_3$ and $R_{3'}$ are as defined in subgroup (6) above, preferably as defined in subgroups (7) to (11), and $R_1$ and $R_{1'}$ are according to preferable embodiment (C).

In preferable subgroup (Ib) of compounds of the invention as defined above, $R_1$ and $R_{1'}$ are both same and represent an optionally substituted, preferably unsubstituted, monocyclic (C5-C7)aryl or (C5-C7)cycloalkyl;

$R_2$ and $R_{2'}$ are same and are both methyl; and $R_3$ and $R_{3'}$ are same and are both optionally substituted branched or straight chain (C6-C50)alkyl, more preferably unsubstituted straight chain (C6-C30)alkyl, such as (C6-C20)alkyl.

A third preferred subgroup (Ic) of compounds (I) is an embodiment (B) as defined above, wherein $R_2$, $R_{2'}$, $R_3$ and $R_{3'}$ are as defined in subgroups (7), (8), (10) or (11) and $R_1$ and $R_{1'}$ are according to preferable embodiment (C) or (D).

In one preferable subgroup (Ic) of compounds of the invention as defined above, $R_1$ and $R_{1'}$ are both same and represent an optionally substituted, preferably unsubstituted, monocyclic (C5-C7)aryl;

$R_2$ and $R_{2'}$ are same and are both optionally substituted branched or straight chain, preferably unsubstituted straight chain, (C6-C50)alkyl, more preferably unsubstituted straight chain (C6-C30)alkyl, such as (C6-C20)alkyl; and $R_3$ and $R_{3'}$ are same and are both optionally substituted branched or straight chain, preferably unsubstituted straight chain, (C6-C50)alkyl, more preferably unsubstituted straight chain (C6-C30)alkyl, such as (C6-C20)alkyl.

In a further preferable subgroup (Id) of compounds (I), $R_1$ and $R_{1'}$ are according to embodiment (D), preferably $R_1$ and $R_{1'}$ are same and are both methyl; and $R_2$ and $R_{2'}$ are same and are both optionally substituted branched or straight chain, preferably unsubstituted straight chain, (C6-C50)alkyl, more preferably unsubstituted straight chain (C6-C30)alkyl, such as (C6-C20)alkyl; and $R_3$ and $R_{3'}$ are same and are both optionally substituted branched or straight chain, preferably unsubstituted straight chain, (C6-C50)alkyl, more preferably unsubstituted straight chain (C6-C30)alkyl, such as (C6-C20)alkyl.

Compounds of subgroup (Ia) is the most preferred group of the above compounds (Ia), (Ib), (Ic) and (Id).

In other preferred embodiments of the invention none of $R_1$-$R_3$ or $R_{1'}$-$R_{3'}$ represents an aromatic group.

In other preferred embodiments, none of $R_1$ to $R_3$ or $R_{1'}$ to $R_{3'}$ represent hydrogen.

Where one or more of $R_1$ to $R_3$ or $R_{1'}$ to $R_{3'}$ represents an aromatic radical this is especially preferably a phenyl group optionally substituted by one to three, such as one, group Z as defined below.

Where one or more of $R_1$ to $R_3$ or $R_{1'}$ to $R_{3'}$ represents a cycloalkyl radical this is especially preferably a cyclohexyl or cyclopentyl group optionally substituted by one to three, such as one, group Z as defined below.

In the compounds of the invention there are preferably no more than two cycloalkyl groups. In further preferred compounds there are no more than two cyclic groups (e.g. carbocyclic, heterocyclic or aromatic groups). In a most preferred embodiment of the invention there are two cyclic groups which each are formed by $R_2$ and $R_3$ together with $C^1$ and by $R_{2'}$ and $R_{3'}$ together with $C^{1'}$.

These preferred embodiments apply to any compound of the invention, in particular any compounds forming part of the sub groups above.

The optional substituents of embodiments (A), (B), (C), (D), (Ia), (Ib), (Ic) and (Id) (and any optional substituent present in the compounds of the invention) are preferably one to four substituents (Z) selected from a saturated or partially unsaturated (C1-C30)hydrocarbyl, a functional group, a saturated or partially unsaturated (C1-C30)hydrocarbyl which optionally bears a functional group as defined above, or from an aromatic hydrocarbyl, which optionally bears a functional group. Preferred substituents (Z) are branched or straight chain (C1-C20)hydrocarbyl or a functional group as defined above. Preferably, no substituted radical should carry more than 1 substituent Z.

Highly preferred substituents (Z) which can be present on any optionally substituted moiety of the compounds of the invention include C1-6 alkyls, especially methyl, ethyl, propyl or tertbutyl; C5-8 cycloalkyl; or phenyl. Where a methyl substituent carries a phenyl side group, the formed group is, of course, benzyl. Where an alkyl substituent carries a cycloalkyl side group, the formed group is, of course, alkyl-cycloalkyl, and so on.

Where a phenyl group carries one substituent it is preferably para to the binding to carbon atom $C^1/C^{1'}$. Where a cyclohexyl group carries one substituent, it is preferably beta to the $C^1/C^{1'}$ carbon atom.

Most Preferred Structures:

The most preferred compounds of the invention are of formula (IV) and (V)

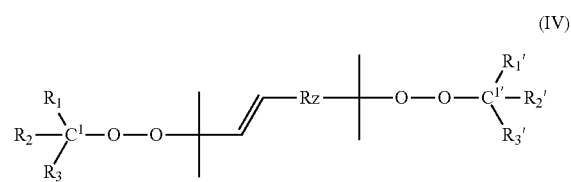

-continued

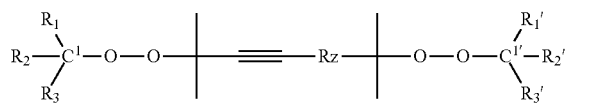
(V)

where the substituents are as hereinbefore defined.
Even further preferred compounds are those of formula (VI)

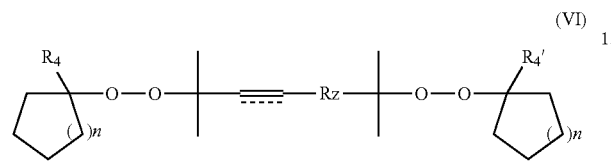
(VI)

wherein Rz is as hereinbefore defined, n is 0 to 3, and then preferably 1 or 2, e.g. forming a cyclopentyl or cyclohexyl group respectively, $R_4$ and $R_{4'}$ each independently represent a branched or straight chain alkyl group having 1 to 30 carbon atoms, preferably methyl or a branched or straight chain alkyl group having 2 to 20, preferably 2 to 12, carbon atoms, more preferably methyl, or a branched or straight chain, preferably straight chain, C6-30 alkyl group;

wherein one or preferably both ring systems independently are unsubstituted or optionally substituted by 1 to 4 substituents Z as defined above. It is most preferred that the ring systems are unsubstituted.

Rz in compounds of formula (IV), (V) and (VI) is preferably a covalent bond.

Further preferred compounds are those of formula (IX) and (X):

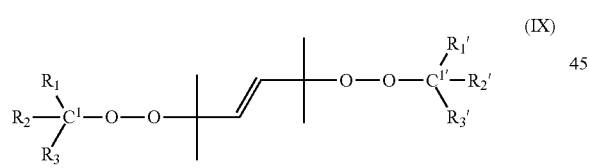
(IX)

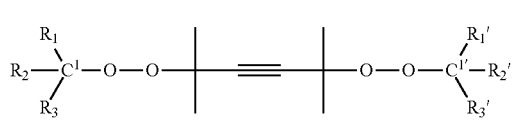
(X)

where the substituents are as hereinbefore defined.

Most preferred compounds of the invention are of formula (VII), more especially of formula (VIII):

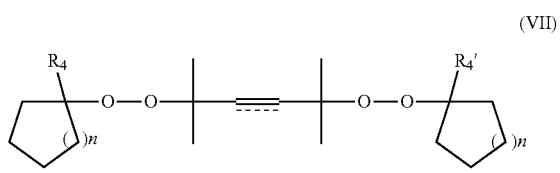
(VII)

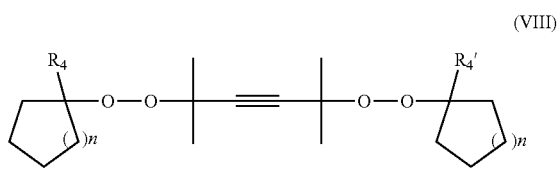
(VIII)

wherein the dotted line, n, and $R_4$ and $R_{4'}$ are as hereinbefore defined.

Preparation of the Compounds of the Invention

Peroxides of formula (I) as defined above can be prepared in several ways, but will be readily prepared by the skilled man analogously or according to the known literature in the chemical field.

Accordingly, compounds of the invention can, as outlined above, be prepared from tertiary alcohols via conversion to a hydroperoxide —OOH type compound. This process allows the preparation of asymmetrical peroxides. Thus for example, a tertiary alcohol can be converted to a tertiary halide and reacted with hydrogen peroxide, perhaps in the presence of a promoter such as silver trifluoroacetate and a non nucleophilic base such as sodium hydrocarbonate to form a tertiary hydroperoxide. This can then be reacted with a linker and a second hydroperoxide introduced in order to allow formation of the other end of the molecule.

Alternatively, and preferably, a starting material for their synthesis is a commercial diol

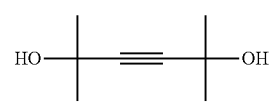

which can be reacted into the corresponding hydroperoxide as reported by N. A. Milas, O. L. Mageli, J. Am. Chem. Soc., 1952, p. 1471

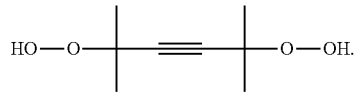

The hydroperoxide can be reacted with additional units of a suitable diol to give compounds of formula (I) of the invention comprising multiple peroxide bonds, giving a building block as exemplified below

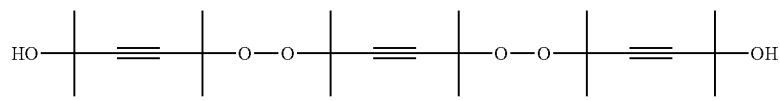

The obtained diol can then be reacted into a suitable peroxide via the corresponding hydroperoxide, as described by N. A. Milas, O. L. Mageli, J. Am. Chem. Soc., 1952, p. 1471.

In general, a hydroperoxide can be reacted with, for example a suitable Hal-C($R_1R_2R_3$) compound or HO—C($R_1R_2R_3$) compound, wherein Hal is a halogen and $R_1$, $R_2$ and $R_3$ as defined above, to give compounds of the invention. The process is commonly catalysed by an acid, such as sulphuric acid or perchloric acid. The reaction can be carried out in a neat media, using one of the components as solvent, or in an organic solvent, or in a two-phase mixture with water.

Equivalent alkenyl compounds can be made by reducing the alkynyl.

In view of the low levels of volatile decomposition products formed during activation of the peroxides of the invention, the present invention reduces or minimises the fire, explosion and health risks in an working environment caused by the use of free radical generating agents compared to the prior art.

End Applications of the Invention

The compounds of the invention are highly useful in applications wherein peroxides are conventionally used, e.g. for various modification methods of polymers via a radical reaction.

The invention is thus also directed to a method for modifying polymers via a radical reaction, wherein the compound(s) of the invention is used as a free radical generating agent. Examples of such modification methods via radical reaction are crosslinking, grafting or visbreaking a polymer.

One preferable embodiment of the modification method of the invention is crosslinking of a polymer by radical reaction using a compound of the invention as defined above. The term "crosslinking" is a well known term and commonly used in the polymer field and means forming, primarily, of interpolymer crosslinks (bridges) via radical reaction. The crosslinked polymer composition has a typical network, i.e. interpolymer crosslinks (bridges), as well known in the field. The decomposition of the compound of the invention and thus the crosslinking step is typically accelerated by using e.g. an elevated temperature. Preferably, the compound of the invention produces no detectable methane or the amount of the produced methane is markedly decreased compared when using dicumyl peroxide in an amount that provides the same crosslinking degree (determined as gel content) as the compound of the invention. The invention further provides a crosslinked polymer composition obtainable by the crosslinking process of the invention.

Another embodiment of the modification method of the invention is the grafting of a polymer by radical reaction using a compound of the invention. The compounds of the invention can be used as free radical generating agents to introduce, via free radical reaction, compounds, which typically bear an unsaturation and a functional group, to a polymer chain. The "grafting of a polymer" is a well known modification method. Grafting may be desired to modify the properties of the polymer, e.g. by subsequently crosslinking the polymer via the functional groups. Such grafting process are described in the literature, e.g. in U.S. Pat. No. 3,646,155 and U.S. Pat. No. 4,117,195. The invention further provides a grafted polymer composition obtainable by the grafting process of the invention.

A further embodiment of the modification method of the invention is visbreaking of a polymer by radical reaction using a free radical generating agent, wherein said free radical generating agent is a compound of the invention. The "visbreaking of a polymer" is a well known modification method for modifying the melt flow rate (MFR) of a polymer. One preferable polymer for visbreaking are homopolymers of propylene, random copolymers of propylene or heterophasic copolymers of propylene. Suitable homo, random and heterophasic polypropylenes (PP) may be produced using common polymerisation processes known in the art. Visbreaking can be carried out in known manner using very well known process and conditions documented in the literature. The invention further provides a visbroken polymer composition obtainable by the visbreaking process of the invention.

The amount of compound of the invention as a free radical generating agent is not critical and depends on the desired degree of modification.

Crosslinking is the most preferred modification method.

The invention is further directed to a polymer composition comprising A) a polymer, and B) a compound of the invention as defined above or in claims.

The invention further provides an article, preferably a cable, comprising the polymer composition of the invention as defined above and below or in claims. Also the preparation process of the article, preferably cable, is provided.

Preferable Embodiments of the End Applications
Polymers for the Invention

In principle, the polymers usable in the modification method, preferably crosslinking process, of the present invention are not limited and can be polymers of any type.

The below description of the preferable polymers is preferred for the polymer composition of the invention and for the crosslinking method of the invention.

A suitable polymer is a polyolefin and can be any conventional polyolefin, in particular which can be used in a layer of a cable, preferably of a power cable.

Suitable polyolefins are, for example, well known and can be commercially available or can be prepared according to or analogously to known polymerization processes described in the chemical literature.

Accordingly, the polyolefin is preferably a polyethylene polymer. Where herein it is referred to a "polymer", e.g. polyolefin, such as polyethylene, this is intended to mean both a homo- and copolymer, e.g. an ethylene homo- and copolymer. The polyolefin copolymer may contain one or more comonomer(s). For polyethylene, ethylene will form the major monomer content present in any polyethylene polymer.

As well known, the term "comonomer" refers to copolymerisable comonomer units.

Where the polyolefin is a copolymer of ethylene with at least one comonomer, then suitable comonomers are selected from non-polar comonomer(s) or polar comonomers, or any mixtures thereof. Preferable non-polar comonomers and polar comonomers are described below in relation to polyethylene produced in a high pressure process. These comonomers can be used in any polyolefin of the invention.

Preferably, the polyolefin is a polyethylene produced in the presence of an olefin polymerisation catalyst or a polyethylene produced in a high pressure process.

"Olefin polymerisation catalyst" means herein preferably a conventional coordination catalyst. It is preferably selected from a Ziegler-Natta catalyst, single site catalyst which term comprises a metallocene and a non-metallocene catalyst, or a chromium catalyst, or any mixture thereof. The terms have a well known meaning.

Polyethylene polymerised in the presence of an olefin polymerisation catalyst is also often called as "low pressure polyethylene" to distinguish it clearly from polyethylene produced under high pressure. Both expressions are well known in the polyolefin field. Low pressure polyethylene can be produced in polymerisation process operating i.a. in bulk, slurry, solution, or gas phase conditions or in any combinations thereof. The olefin polymerisation catalyst is typically a coordination catalyst.

More preferably, the polyolefin is selected from a homopolymer or a copolymer of ethylene produced in the presence of a coordination catalyst or produced in a high pressure polymerisation process.

Where the polyolefin is a low pressure polyethylene (PE), then such low pressure PE is preferably selected from a very low density ethylene copolymer (VLDPE), a linear low density ethylene copolymer (LLDPE), a medium density ethylene copolymer (MDPE) or a high density ethylene homopolymer or copolymer (HDPE). These well known types are named according to their density area. The term VLDPE includes herein polyethylenes which are also known as plastomers and elastomers and covers the density range of from 850 to 909 kg/m$^3$. The LLDPE has a density of from 909 to 930 kg/m$^3$, preferably of from 910 to 929 kg/m$^3$, more preferably of from 915 to 929 kg/m$^3$. The MDPE has a density of from 930 to 945 kg/m$^3$, preferably 931 to 945 kg/m$^3$. The HDPE has a density of more than 945 kg/m$^3$, preferably of more than 946 kg/m$^3$, preferably from 946 to 977 kg/m$^3$, more preferably from 946 to 965 kg/m$^3$.

More preferably, such low pressure copolymer of ethylene for the polyolefin is copolymerized with at least one comonomer selected from C3-20 alpha olefin, more preferably from C4-12 alpha-olefin, more preferably from C4-8 alpha-olefin, e.g. with 1-butene, 1-hexene or 1-octene, or a mixture thereof. The amount of comonomer(s) present in a PE copolymer is from 0.1 to 15 mol %, typically 0.25 to 10 mol-%.

Moreover, where the polyolefin is a low pressure PE polymer, then such PE can be unimodal or multimodal with respect to molecular weight distribution (MWD=Mw/Mn). Generally, a polymer comprising at least two polymer fractions, which have been produced under different polymerization conditions (including i.a. any of the process parameters, feeds of starting materials, feeds of process controlling agents and feeds of catalyst systems) resulting in different (weight average) molecular weights and molecular weight distributions for the fractions, is referred to as "multimodal". The prefix "multi" relates to the number of different polymer fractions present in the polymer. Thus, for example, multimodal polymer includes so called "bimodal" polymer consisting of two fractions. The form of the molecular weight distribution curve, i.e. the appearance of the graph of the polymer weight fraction as a function of its molecular weight, of a multimodal polymer will show two or more maxima or is typically distinctly broadened in comparison with the curves for the individual fractions.

Unimodal low pressure PE can be produced by a single stage polymerisation in a single reactor in a well known and documented manner. The multimodal (e.g. bimodal) low pressure PE can be produced e.g. by blending mechanically together two or more separate polymer components or, preferably, by in-situ blending during the polymerisation process of the components. Both mechanical and in-situ blending are well known in the field. In-situ blending means the polymerisation of the polymer components under different polymerisation conditions, e.g. in a multistage, i.e. two or more stage, polymerization or by the use of two or more different polymerization catalysts, in a one stage polymerization, or by use a combination of multistage polymerisation and two or more different polymerisation catalysts. The polymerisation zones may operate in bulk, slurry, solution, or gas phase conditions or in any combinations thereof, as known in the filed.

According to a second embodiment the polyolefin is a polyethylene produced in a high pressure polymerisation process, preferably by radical polymerisation in the presence of an initiator(s). More preferably the polyolefin is a low density polyethylene (LDPE). It is to be noted that a polyethylene produced in a high pressure (HP) is referred herein generally as LDPE and which term has a well known meaning in the polymer field. Although the term LDPE is an abbreviation for low density polyethylene, the term is understood not to limit the density range, but covers the LDPE-like HP polyethylenes with low, medium and higher densities. The term LDPE describes and distinguishes only the nature of HP polyethylene with typical features, such as high branching degree, compared to the PE produced in the presence of an olefin polymerisation catalyst.

The preferred polyolefin is according to the second embodiment and is an LDPE polymer which may be a low density homopolymer of ethylene (referred herein as LDPE homopolymer) or a low density copolymer of ethylene with one or more comonomer(s) (referred herein as LDPE copolymer). The one or more comonomers of LDPE copolymer are preferably selected from the polar comonomer(s), non-polar comonomer(s) or from a mixture of the polar comonomer(s) and non-polar comonomer(s), as defined below. Moreover, said LDPE homopolymer or LDPE copolymer as said polyolefin may optionally be unsaturated.

As a polar comonomer for the LDPE copolymer as said polyolefin, comonomer(s) containing hydroxyl group(s), alkoxy group(s), carbonyl group(s), carboxyl group(s), ether group(s) or ester group(s), or a mixture thereof, can be used. More preferably, comonomer(s) containing carboxyl and/or ester group(s) are used as said polar comonomer. Still more preferably, the polar comonomer(s) of LDPE copolymer is selected from the groups of acrylate(s), methacrylate(s) or acetate(s), or any mixtures thereof. If present in said LDPE copolymer, the polar comonomer(s) is preferably selected from the group of alkyl acrylates, alkyl methacrylates or vinyl acetate, or a mixture thereof. Further preferably, said polar comonomers are selected from $C_1$- to $C_6$-alkyl acrylates, $C_1$- to $C_6$-alkyl methacrylates or vinyl acetate. Still more preferably, said polar LDPE copolymer is a copolymer of ethylene with $C_1$- to $C_4$-alkyl acrylate, such as methyl, ethyl, propyl or butyl acrylate, or vinyl acetate, or any mixture thereof.

As the non-polar comonomer(s) for the LDPE copolymer, comonomer(s) other than the above defined polar comonomers can be used. Preferably, the non-polar comonomers are other than comonomer(s) containing hydroxyl group(s), alkoxy group(s), carbonyl group(s), carboxyl group(s), ether group(s) or ester group(s). One group of preferable non-polar comonomer(s) comprise, preferably consist of, monounsaturated (= One double bond) comonomer(s), preferably olefins, preferably alpha-olefins, more preferably $C_3$ to $C_{10}$ alpha-olefins, such as propylene, 1-butene, 1-hexene, 4-methyl-1-pentene, styrene, 1-octene, 1-nonene; polyunsaturated (= more than one double bond) comonomer(s); a silane group containing comonomer(s); or any mixtures thereof. The polyunsaturated comonomer(s) are further described below in relation to unsaturated LDPE copolymers.

If the LDPE polymer is a copolymer, it preferably comprises 0.001 to 50 wt.-%, more preferably 0.05 to 40 wt.-%, still more preferably less than 35 wt.-%, still more preferably less than 30 wt.-%, more preferably less than 25 wt.-%, of one or more comonomer(s).

Typically, and preferably in wire and cable (W&C) applications, the density of the polyolefin, preferably of the LDPE polymer, is higher than 860 kg/m$^3$. Preferably the density of the polyolefin, preferably of the LDPE homopolymer or copolymer, is not higher than 960 kg/m$^3$, and preferably is from 900 to 945 kg/m$^3$. The MFR$_2$ (2.16 kg, 190° C.) of the polyolefin, preferably of the LDPE polymer, is preferably from 0.01 to 50 g/10 min, more preferably from 0.01 to 30.0 g/10, more preferably is from 0.1 to 20 g/10 min, and most preferably is from 0.2 to 10 g/10 min.

The polyolefin, more preferably the polyethylene polymer, more preferably the LDPE polymer, may optionally be unsaturated, i.e. the polyolefin, preferably the LDPE polymer, may comprise carbon-carbon double bonds (—C=C—). The "unsaturated" means herein that the polyolefin, contains carbon-carbon double bonds/1000 carbon atoms in a total amount of at least 0.4/1000 carbon atoms.

If an LDPE homopolymer is unsaturated, then the unsaturation can be provided e.g. by a chain transfer agent (CTA), such as propylene, and/or by polymerization conditions. If an LDPE copolymer is unsaturated, then the unsaturation can be provided by one or more of the following means: by a chain transfer agent (CTA), by one or more polyunsaturated comonomer(s) or by polymerisation conditions. It is well known that selected polymerisation conditions such as peak temperatures and pressure, can have an influence on the unsaturation level. In case of an unsaturated LDPE copolymer, it is preferably an unsaturated LDPE copolymer of ethylene with at least one polyunsaturated comonomer, and optionally with other comonomer(s), such as polar comonomer(s) which is preferably selected from acrylate or acetate comonomer(s). More preferably an unsaturated LDPE copolymer is an unsaturated LDPE copolymer of ethylene with at least polyunsaturated comonomer(s).

The polyunsaturated comonomers suitable for the unsaturated polyolefin preferably consist of a straight carbon chain with at least 8 carbon atoms and at least 4 carbons between the non-conjugated double bonds, of which at least one is terminal, more preferably, said polyunsaturated comonomer is a diene, preferably a diene which comprises at least eight carbon atoms, the first carbon-carbon double bond being terminal and the second carbon-carbon double bond being non-conjugated to the first one. Preferred dienes are selected from $C_8$ to $C_{14}$ non-conjugated dienes or mixtures thereof, more preferably selected from 1,7-octadiene, 1,9-decadiene, 1,11-dodecadiene, 1,13-tetradecadiene, 7-methyl-1,6-octadiene, 9-methyl-1,8-decadiene, or mixtures thereof. Even more preferably, the diene is selected from 1,7-octadiene, 1,9-decadiene, 1,11-dodecadiene, 1,13-tetradecadiene, or any mixture thereof, however, without limiting to above dienes.

It is well known that e.g. propylene can be used as a comonomer or as a chain transfer agent (CTA), or both, whereby it can contribute to the total amount of the carbon-carbon double bonds, preferably to the total amount of the vinyl groups. Herein, when a compound which can also act as comonomer, such as propylene, is used as CTA for providing double bonds, then said copolymerisable comonomer is not calculated to the comonomer content.

If the polyolefin, more preferably the LDPE polymer, is unsaturated, then it has preferably a total amount of carbon-carbon double bonds, which originate from vinyl groups, vinylidene groups and trans-vinylene groups, if present, of more than 0.4/1000 carbon atoms, preferably of more than 0.5/1000 carbon atoms. The upper limit of the amount of carbon-carbon double bonds present in the polyolefin is not limited and may preferably be less than 5.0/1000 carbon atoms, preferably less than 3.0/1000 carbon atoms.

In some embodiments, for example where a higher crosslinking level is desired, the total amount of carbon-carbon double bonds, which originate from vinyl groups, vinylidene groups and trans-vinylene groups, if present, in the unsaturated LDPE, is preferably higher than 0.40/1000 carbon atoms, preferably higher than 0.50/1000 carbon atoms, preferably higher than 0.60/1000 carbon atoms.

More preferably, if the polyolefin is an unsaturated LDPE, then it is an unsaturated LDPE as defined above and contains at least vinyl groups and the total amount of vinyl groups is preferably higher than 0.05/1000 carbon atoms, still more preferably higher than 0.08/1000 carbon atoms, and most preferably of higher than 0.11/1000 carbon atoms. Preferably, the total amount of vinyl groups is of lower than 4.0/1000 carbon atoms. More preferably, the polyolefin, if unsaturated, contains, prior to crosslinking, vinyl groups in total amount of more than 0.15/1000 carbon atoms, preferably of more than 0.20/1000 carbon atoms, preferably of more than 0.25/1000 carbon atoms still more preferably of more than 0.30/1000 carbon atoms.

In one preferable embodiment the polyolefin is a saturated polyethylene polymer, preferably a saturated LDPE polymer as defined above, which contains carbon-carbon double bonds/1000 carbon atoms in a total amount of less than 0.4/1000 carbon atoms, as defined above.

In another equally preferable embodiment the polyolefin is an unsaturated polyethylene polymer, preferably an unsaturated LDPE polymer as defined above, which contains at least 0.4 carbon-carbon double bonds/1000 carbon atoms as defined above. In this embodiment the unsaturated LDPE polymer is preferably an unsaturated LDPE homopolymer or an unsaturated LDPE copolymer of ethylene with at least one polyunsaturated comonomer, preferably a diene as defined above, and optionally with other comonomer(s), and has the total amount of carbon-carbon double bonds, which originate from vinyl groups, vinylidene groups and trans-vinylene groups, if present, as defined above, preferably has the total amount of vinyl groups as defined above.

Said saturated and unsaturated polyethylene polymers, preferably saturated and unsaturated LDPE copolymers are both highly usable for the invention for use as the polyolefin of a polymer composition, preferably in a layer, preferably a crosslinkable layer, of a power cable.

Accordingly, the polyolefin of the invention is preferably a LDPE polymer, which is preferably produced at high pressure by free radical initiated polymerisation (referred to as high pressure (HP) radical polymerization). The HP reactor can be e.g. a well known tubular or autoclave reactor or a combination thereof, preferably a tubular reactor. The high pressure (HP) polymerisation and the adjustment of process conditions for further tailoring the other properties of the polyolefin depending on the desired end application are well known and described in the literature, and can readily be used by a skilled person. Suitable polymerisation temperatures range up to 400° C., preferably from 80 to 350° C. and pressure from 70 MPa, preferably 100 to 400 MPa, more preferably from 100 to 350 MPa. Pressure can be measured at least after compression stage and/or after the tubular reactor. Temperature can be measured at several points during all steps.

After the separation the obtained LDPE is typically in a form of a polymer melt which is normally mixed and pelletized in a pelletising section, such as pelletising extruder, arranged in connection to the HP reactor system. Optionally, additive(s), such as antioxidant(s), can be added in this mixer in a known manner.

Further details of the production of ethylene (co)polymers by high pressure radical polymerization can be found i.a. in the Encyclopedia of Polymer Science and Engineering, Vol. 6 (1986), pp 383-410 and Encyclopedia of Materials: Science and Technology, 2001 Elsevier Science Ltd.: "Polyethylene: High-pressure, R. Klimesch, D. Littmann and F.-O. Mailing pp. 7181-7184.

When an unsaturated LDPE copolymer of ethylene is prepared, then, as well known, the carbon-carbon double bond content can be adjusted by polymerising the ethylene e.g. in the presence of one or more polyunsaturated comonomer(s), chain transfer agent(s), or both, using the desired feed ratio between monomer, preferably ethylene, and polyunsaturated comonomer and/or chain transfer agent, depending on the nature and amount of C—C double bonds desired for the unsaturated LDPE copolymer. I.a. WO 9308222 describes a high pressure radical polymerisation of ethylene with polyunsaturated monomers. As a result the unsaturation can be uniformly distributed along the polymer chain in random copolymerisation manner. Also e.g. WO 9635732 describes high pressure radical polymerisation of ethylene and a certain type of polyunsaturated α,ω-divinylsiloxanes.

Polymer Composition of the Invention

The invention also provides a polymer composition comprising
A) a polymer, e.g. polyolefin, and
B) a compound of the invention as hereinbefore defined.

The invention thus provides also a polymer composition comprising a compound of the invention as defined above and polyolefin, preferably as hereinbefore defined. Also a process for producing a polymer composition is provided, wherein the compound of the invention is added to a polymer composition.

The amount of the compound of the invention in the polymer composition can naturally vary depending on the desired modification method. The amount of the compound of the invention as a free radical generating agent used for the crosslinking is not critical and can vary depending on the desired crosslinking degree and the type of the crosslinkable polymer. As an example only, the amount of the compound of the invention as said free radical generating agent may be less than 10.0 wt %, less than 6.0 wt %, less than 5.0 wt %, less than 3.5 wt %, e.g. between 0.1 to 3.0 wt %, such as 0.2 to 2.6 wt %, based on the weight of the polymer composition.

Moreover, the polymer composition of the invention may additionally, comprise further free radical generating agent(s), such as another compound of the invention.

Moreover, the polymer composition of the invention may further contain other components, such as further polymer component(s), additive(s) or any mixtures thereof.

In one preferable embodiment of the polymer composition of the invention said polymer composition further comprises additives. As an example only such additives include one or more of antioxidants, stabilisers, processing aids, scorch retardants, crosslinking boosters or water tree retardants, or any mixtures thereof. As antioxidant, sterically hindered or semi-hindered phenols, optionally substituted with functional group(s), aromatic amines, aliphatic sterically hindered amines, organic phosphates, thio compounds, and mixtures thereof, can be mentioned. Typical cross-linking boosters may include compounds having a vinyl or an allyl group, e.g. triallylcyanurate, triallylisocyanurate, and di-, tri- or tetra-acrylates. As further additives, flame retardant additives, acid scavengers, fillers, such as carbon black, and voltage stabilizers can be mentioned. All the above mentioned additives are well known in polymer field. Such compositions are very useful for wire and cable applications, such as for cables of the invention discussed below.

The polymer composition may optionally be unsaturated, i.e. the polymer composition may comprise carbon-carbon double bonds (—C=C—). The "unsaturated" means herein that the polymer composition contains carbon-carbon double bonds/1000 carbon atoms in a total amount of at least 0.4/1000 carbon atoms.

The unsaturation can be provided to the polymer composition i.a. by means of a low molecular weight (Mw) compound(s) (species), such as crosslinking booster(s) or scorch retarder additive(s), or any combinations thereof. The total amount of double bonds means herein double bonds determined from the source(s) that are known and deliberately added to contribute to the unsaturation. If two or more above sources of double bonds are chosen to be used for providing the unsaturation, then the total amount of double bonds in the polymer composition means the sum of the double bonds present in the double-bond sources. It is evident that a characteristic model compound for calibration is used for each chosen source to enable the quantitative infrared (FTIR) determination.

Any double bond measurements are carried out prior to optional crosslinking.

If the polymer composition is unsaturated (prior to optional crosslinking), then it is preferred that the unsaturation originates at least from an unsaturated polyolefin component. More preferably, the unsaturated polyolefin is an unsaturated polyethylene, more preferably an unsaturated LDPE polymer, even more preferably an unsaturated LDPE homopolymer or an unsaturated LDPE copolymer as hereinbefore defined. When polyunsaturated comonomer(s) are present in the LDPE polymer as said unsaturated polyolefin, then the LDPE polymer is an unsaturated LDPE copolymer.

In a preferred embodiment the term "total amount of carbon-carbon double bonds" is defined from the unsaturated polyolefin, and refers, if not otherwise specified, to the combined amount of double bonds which originate from vinyl groups, vinylidene groups and trans-vinylene groups, if present. Naturally the polyolefin does not necessarily contain all the above three types of double bonds. However, any of the three types, when present, is calculated to the "total amount of carbon-carbon double bonds". The amount of each type of double bond is measured as indicated under "Determination methods".

The polymer composition of the invention can be in a well known powder, grain or pellet form. Pellets mean herein generally any polymer product which is formed from reactor-made polymer (obtained directly from the reactor) by post-reactor modification to a solid polymer particles. A well-known post-reactor modification process is pelletising a meltmix of a polymer component(s) and optional additive(s) in pelletising equipment to form solid pellets. Pellets can be of any size and shape.

The compound (I) of the invention can be incorporated into the polymer, e.g. polymer pellets, to form a product, preferably a pellet product, wherein the product, preferably pellet product, comprises the polymer component together with the compound of the invention. The compound of the invention can be incorporated into polymer e.g. by meltmixing with polymer and by pelletizing the obtained meltmix or by impregnating the compound of the invention into the solid polymer pellets. The obtained (pellet) product can then be introduced into a product production step, such as cable production step.

Alternatively, the polyolefin and the compound of the invention can be provided separately, e.g. the compound of the invention can be provided in a well known master batch, to the article production process, preferably cable production process, and combined with the polymer component during the production process.

All or part of the optional other component(s), such as further polymer component(s) or additive(s) can be present in the polymer composition before introducing to the article preparation process or can be added, e.g by an article producer, during the article production process.

Most preferably, the polymer composition of the invention is provided to the cable production process in a suitable product form, such as a pellet product. Preferably, if present, the optional other component(s) are also already provided in such product together with the polymer component and the compound of the invention.

Cable of the Invention

In one preferable embodiment said article of the invention is a crosslinkable cable which comprises a conductor which is surrounded by one or more layers, wherein at least one layer comprises a polymer composition of the invention.

The term "conductor" means herein above and below that the conductor comprises one or more wires. Moreover, the cable may comprise one or more such conductors. Preferably the conductor is an electrical conductor.

In one embodiment of the cable of the invention at least one layer is an insulation layer which comprises said polymer composition of the invention. Thus, viewed from another aspect the invention provides a crosslinkable cable which comprises at least one insulation layer comprising a polymer composition of the invention.

In another embodiment of the cable of the invention at least one layer is a semiconductive layer comprising said polymer composition of the invention. "Semiconductive layer" means herein that said layer comprises carbon black and has a volume resistivity of 100 000 Ω-cm or below when measured at 23° C. or 90° C., or, when measured according to ISO 3915 using a plaque, has a volume resistivity of 100 Ω-cm or below at 23° C., or of 1000 Ω-cm or below at 90° C. Thus, viewed from another aspect the invention provides a crosslinkable cable which comprises at least one semiconductive layer comprising a polymer composition of the invention.

In further embodiment, the cable of the invention comprises a jacketing layer and optionally one or more layers selected from an insulation layer and semiconductive layer surrounded by said jacketing layer, wherein said jacketing layer comprises said polymer composition of the invention.

The crosslinkable cable of the invention may be a low voltage cable comprising a conductor surrounded by an insulation layer and optionally a jacketing layer, wherein at least one layer, preferably at least said insulation layer comprises a polymer composition of the invention; or a power cable comprising an electrical conductor surrounded by one or more layers comprising at least an inner semiconductive layer, insulation layer and an outer semiconductive layer, in that order, and optionally surrounded by a jacketing layer, wherein at least one of said layers comprises a polymer composition of the invention.

In the above power cable embodiment of the invention, the layer comprising the polymer composition is preferably selected from an insulation layer or a semiconductive layer, more preferably at least from insulation layer.

In the context of the present invention, a low voltage cable is a cable operating in voltages 1 kV or below. A power cable is defined to be a cable transferring energy operating at any voltage, typically operating at voltages higher than 1 kV. The voltage applied to the power cable can be alternating (AC), direct (DC), or transient (impulse). In a preferred embodiment, the power cable prepared according to the present invention is operating at voltages higher than 6 kV and are known i.a. as medium voltage (MV), high voltage (HV) and extra high voltage (EHV) power cables, which terms have well known meaning and indicate the operating level of such cable.

Said outer semiconductive layer of said power cable of the invention can be non-strippable, i.e. bonded and non-peelable, or strippable, i.e. non-bonded and peelable. Said terms have well known meanings in the wire and cable field.

Preparation Process for Producing a Cable

A preferable embodiment of the process for preparing an article of the invention is a process for producing a cable comprising steps of applying, preferably by (co)extrusion, one or more layers on a conductor, wherein at least one layer comprises said polymer composition of the invention.

The term "(co)extrusion" means herein that in case of two or more layers, said layers can be extruded in separate steps, or at least two or all of said layers can be coextruded in a same extrusion step, as well known in the art. The cable production process comprises the steps of mixing, preferably meltmixing in an extruder, a polymer composition of the invention for at least one layer of a cable; and applying the obtained (melt)mix on a conductor, preferably by coextrusion, to form at least one layer of the resulting cable.

Meltmixing means mixing above the melting point of at least the major polymer component(s) of the obtained mixture and is carried out for example, at a temperature of at least 15° C. above the melting or softening point of polymer component(s).

In said cable production process of the invention the polymer composition can mixed in a cable extruder in a separate mixer before being introduced to the extruder for producing said layers or the cable production process may optionally comprise a separate mixing step, e.g. in a mixer arranged in connection and preceding the cable extruder of the cable production line. Mixing in the preceding separate mixer can be carried out by mixing with or without external heating (heating with an external source) of the component(s).

Also all or part of the optional further component(s) (e.g. further polymer component(s) and/or further additive(s)), can be combined with the polymer component and optionally with the compound of the invention prior to or during the extrusion ((melt)mixing).

Most preferably, the polymer composition of the invention is introduced to the cable production process in form of pellets comprising at least the polymer component together with the compound of the invention.

Typically the cable of the invention is crosslinked after the formation of cable layers. The cable production process preferably comprises:

applying one or more layers comprising the polymer composition of the invention on a conductor, crosslinking by radical reaction said at least one layer.

The crosslinking occurs in the presence of the compound of the invention by radical reaction.

The obtained, preferably crosslinked, cable is then recovered the crosslinked cable in a conventional manner for further use.

In above crosslinking process of the invention crosslinking conditions can vary depending i.a. on the used materials and cable size. The crosslinking of the invention is effected e.g. in a known manner preferably in an elevated temperature. Preferably the lowest temperature in a cable layer during the crosslinking step is above 140° C., more preferably above 150° C. The crosslinking may be carried out in a liquid or gas medium, such as in an inert gas, such as $N_2$, atmosphere. The pressure during the crosslinking step of the invention is typically up to 20 bar in inert atmosphere.

A further preferable embodiment of the crosslinking process of the invention comprises a further step of cooling the crosslinked cable preferably under pressurized conditions in a cooling medium e.g. in gas or liquid, such as $N_2$, oil or water.

The cooling is effected in a cooling zone, which may be optionally integrated with the preceding crosslinking zone, e.g. in a known vulcanization tube.

The crosslinking and cooling step is normally carried out under pressurized conditions to prevent the formation of voids due to volatile decomposition products of e.g. peroxides.

Optionally, if desired, the crosslinked cable of the invention may be subjected to an additional non-pressurised cooling step after said pressurized cooling step, for further cooling of the cable.

The cable preparation process of the invention optionally comprises a further recovering step of the cable coming from the cooling step. Recovering may be effected by winding the cable on a cable drum in a known manner.

In a further embodiment of the process of the invention the cable obtained from the cooling step and optionally recovered, e.g. wound to a cable drum, may optionally be subjected, if needed in some applications, to a subsequent degassing step i.a. for removing or reducing any volatile decomposition products possibly resulting from said crosslinking step of the invention. In said degassing step the cable of the invention is preferably exposed either in ambient or elevated temperature for a period of time. As an example only, said degassing temperature may be e.g. 50-80° C. In one embodiment of the crosslinking process said degassing step may be shortened considerably or even avoided due to decreased level of said volatile by-products.

The cable of the invention produced by the above process of the invention may finally be further processed, e.g. protected with a protective layer, and/or optionally covered by a jacketing layer in a subsequent finishing step in a known manner and recovered for the end use thereof.

The invention thus provides also a crosslinked cable comprising crosslinked polymer composition as defined above, preferably a crosslinked low voltage cable or power cable, more preferably a crosslinked power cable, as defined above. Preferably said crosslinked cable is obtainable by any of the crosslinking process as defined above.

In one preferable embodiment of a crosslinking process of the invention a crosslinked power cable is produced which is selected from a crosslinked LV, MV or HV, including EHV, cable.

Due to the compounds of the invention the amount of voids in polymer products, such as cable layers can be reduced or even avoided, since less volatile decomposition products are formed from e.g. when the compound of the invention is used for modifying the polymer. Moreover, the invention also enables to improve the processability of a cable, i.a. in terms of safer and faster processing. E.g. the crosslinking process of the invention can be faster and/or more economical, since both cooling and/or degassing steps may be carried out in a reduced time and/or in a less energy consuming manner, if desired.

Determination Methods

Unless otherwise stated the below determination methods were used to determine the properties defined generally in the description part and claims and in the experimental part.
Wt %:
 % by weight Melt Flow Rate:
The melt flow rate (MFR) is determined according to ISO 1133 and is indicated in g/10 min. The MFR is an indication of the flowability, and hence the processability, of the polymer. The higher the melt flow rate, the lower the viscosity of the polymer. The MFR is determined at 190° C. for polyethylenes and may be determined at different loadings such as 2.16 kg ($MFR_2$) or 21.6 kg ($MFR_{21}$). The MFR is determined at 230° C. for polypropylenes.

Density:
Low density polyethylene (LDPE): The density was measured according to ISO 1183-2. The sample preparation was executed according to ISO 1872-2 Table 3 Q (compression moulding).

Low pressure process polyethylene: Density of the polymer was measured according to ISO 1183/1872-2B.

A) Quantification of the Amount of Carbon-Carbon Double Bonds by IR Spectroscopy Quantitative infrared (IR) spectroscopy was used to quantify the amount of carbon-carbon double bonds (C═C). Calibration was achieved by prior determination of the molar extinction coefficient of the C═C functional groups in representative low molecular weight model compounds of known structure.

The amount of each of these groups (N) was determined as number of carbon-carbon double bonds per thousand total carbon atoms (C═C/1000 C) via:

$$N=(A\times14)/(E\times L\times D)$$

were A is the maximum absorbance defined as peak height, E the molar extinction coefficient of the group in question ($l \cdot mol^{-1} \cdot mm^{-1}$), L the film thickness (mm) and D the density of the material ($g \cdot cm^{-1}$).

The total amount of C═C bonds per thousand total carbon atoms can be calculated through summation of N for the individual C═C containing components.

For polyethylene samples solid-state infrared spectra were recorded using a FTIR spectrometer (Perkin Elmer 2000) on compression moulded thin (0.5-1.0 mm) films at a resolution of 4 $cm^{-1}$ and analysed in absorption mode.

1) Polymer Compositions Comprising Polyethylene Homopolymers and Copolymers, Except Polyethylene Copolymers with >0.4 Wt % Polar Comonomer For polyethylenes three types of C═C containing functional groups were quantified, each with a characteristic absorption and each calibrated to a different model compound resulting in individual extinction coefficients:

vinyl (R—CH═CH2) via 910 $cm^{-1}$ based on 1-decene [dec-1-ene] giving E=13.13 $l \cdot mol^{-1} \cdot mm^{-1}$ vinylidene (RR'C═CH2) via 888 $cm^{-1}$ based on 2-methyl-1-heptene[2-methyhept-1-ene] giving E=18.24 $l \cdot mol^{-1} \cdot mm^{-1}$ trans-vinylene (R—CH═CH—R') via 965 $cm^{-1}$ based on trans-4-decene[(E)-dec-4-ene] giving E=15.14 $l \cdot mol^{-1} \cdot mm^{-1}$ For polyethylene homopolymers or copolymers with <0.4 wt % of polar comonomer linear baseline correction was applied between approximately 980 and 840 $cm^{-1}$.

2) Polymer Compositions Comprising Polyethylene Copolymers with >0.4 Wt % Polar Comonomer For polyethylene copolymers with >0.4 wt % of polar comonomer two types of C═C containing functional groups were quantified, each with a characteristic absorption and each calibrated to a different model compound resulting in individual extinction coefficients:

vinyl (R—CH═CH2) via 910 $cm^{-1}$ based on 1-decene [dec-1-ene] giving E=13.13 $l \cdot mol^{-1} \cdot mm^{-1}$ vinylidene (RR'C=CH2) via 888 cm$^{-1}$ based on 2-methyl-1-heptene[2-methyl-hept-1-ene] giving E=18.24 l·mol$^{-1}$·mm$^{-1}$

EBA:

For poly(ethylene-co-butylacrylate) (EBA) systems linear baseline correction was applied between approximately 920 and 870 cm$^{-1}$.

EMA:

For poly(ethylene-co-methylacrylate) (EMA) systems linear baseline correction was applied between approximately 930 and 870 cm$^{-1}$.

3) Polymer Compositions Comprising Unsaturated Low Molecular Weight Molecules

For systems containing low molecular weight C=C containing species direct calibration using the molar extinction coefficient of the C=C absorption in the low molecular weight species itself was undertaken.

B) Quantification of Molar Extinction Coefficients by IR Spectroscopy

The molar extinction coefficients were determined according to the procedure given in ASTM D3124-98 and ASTM D6248-98. Solution-state infrared spectra were recorded using a FTIR spectrometer (Perkin Elmer 2000) equipped with a 0.1 mm path length liquid cell at a resolution of 4 cm$^{-1}$.

The molar extinction coefficient (E) was determined as l·mol$^{-1}$·mm$^{-1}$ via:

$$E=A/(C\times L)$$

where A is the maximum absorbance defined as peak height, C the concentration (mol·l$^{-1}$) and L the cell thickness (mm).

At least three 0.18 mol·l$^{-1}$ solutions in carbondisulphide (CS$_2$) were used and the mean value of the molar extinction coefficient determined.

Gel Content

The gel content was determined according to ASTM D 2765-01, method A using decaline extraction and using a crosslinked sample which consists of the polymer composition under test and prepared according to "Preparation of samples for Gel Content and for GC-Analysis protocol" as described below.

GC-Analysis Protocol

In definitions in the description and in experimental part the volatile, e.g. CH$_4$, content given in ppm (weight) is determined by gas chromatography (GC) from a crosslinked sample which is prepared according to "Preparation of samples for Gel Content and for GC-Analysis protocol" as described below The test is used to determine the produced volatiles, e.g. methane, content of a free radical generating agent. The test free radical generating agent is used in such an amount with which a crosslinking degree expressed as gel content of 50% was achieved, preferably gel content of at least 50%.

The collection of volatiles from said sample specimen (to a head space bottle, see below) is started within one hour after the modification step is stopped.

The test sample (specimen) is placed in a 120 ml head space bottle with an aluminium crimp cup with seal and heat treated at 60° C. for 1.5 h for collecting any gaseous volatiles present in said sample. Then 0.3-0.5 ml of the gas captured in the sample bottle is injected into a gas chromatograph, wherein the presence and content of the volatiles, e.g. methane, which are desired to be measured in a known manner. Double samples are analysed and a "zero-sample" without free radical generating agent/modification is used as a reference. The instrument used herein was a Varian 3400 with a Al$_2$O$_3$/Na$_2$SO$_4$-column of 0.53 mm×50 m, supplied by Chrompack. The volatile, e.g. CH$_4$, content given in ppm (weight).

Preparation of Samples for Gel Content and for GC-Analysis Protocol

The pellets of the polymer for test composition were ground to a fine powder in a Retsch grinder with a 1.5 mm sieve. The powder obtained was impregnated with the test peroxide dissolved in a pentane solution until the pentane had evaporated to give a dry powder of the test peroxide and the test polymer.

For the gel content measurement, 1.5 wt % of the test compound of the invention (inventive peroxide 1), 1.7% of the inventive peroxide 2 or, unless otherwise stated, 1.5 wt % of the reference peroxide were added to the test polymer.

For the GC-Analysis protocol (volatile determination), 2 wt %, 1.7 wt % or 1.5 wt % of the test compounds of the invention (inventive peroxides) or the reference peroxide were added to the test polymer. Wt % of peroxide is based on the total amount of the polymer composition.

For the gel content measurement, test plaques of 100 mm long, 100 mm wide, and 0.1 mm thick were prepared. For the GC-Analysis protocol (volatile determination), test plaques of 100 mm long, 100 mm wide, and 1.5 mm thick were prepared. The test plaque preparation was conducted in a Specac press, where the composition was kept at 120° C. for 1 min at 5 bar, then the temperature was increased with 60° C./min for 1 min to reach 180° C. at 5 bar, and kept at 180° C. at 5 bar for 12 min, followed by cooling to ambient temperature over 30 min at 5 bar. The test plaques were crosslinked during the plaque preparation procedure.

EXPERIMENTAL PART

Components of Test Polymer Compostions

Example 1

Compound I of the Invention, Inventive Peroxide 1

Preparation of 2,5-dimethyl-2,5-di(1-methylcyclopentylperoxy)hex-3-yne

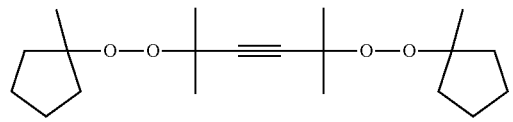 [SMILES: CC(C)(C#CC(C)(C)OOC1(C)CCCC1)OOC1(C)CCCC1]

A round-bottom flask was charged with 1-methylcyclopentanol (17.7 g, 0.177 mol) and warmed to 40° C. HClO$_4$ (1.38 mL, 0.016 mol) was added drop-wise over 10 minutes followed by 2,5-Dimethyl-2,5-dihydroperoxyhexyne-3 (14 g, 0.08 mol). The reaction mixture was stirred at 40° C. for 2 hours. The reaction mixture was washed with brine. The organic layer was dried over anhydrous MgSO$_4$, filtered and concentrated to afford the crude material, which was purified by chromatography to give 4.9 g 2,5-dimethyl-2,5-di(1-methylcyclopentylperoxy)hex-3-yne. $^{13}$C-NMR δ 24.79, 25.12, 27.50, 37.42, 74.56, 85.79, 90.60.

Example 2

Compound 2 of the Invention, Inventive Peroxide 2

Preparation of 2,5-dimethyl-2,5-di(1-methylcyclohexylperoxy)hex-3-yne

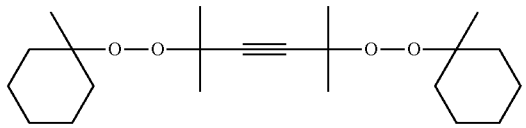 [SMILES: CC(C)(C#CC(C)(C)OOC1(C)CCCCC1)OOC1(C)CCCCC1]

A round-bottom flask was charged with 1-methyl-cyclohexanol (23 g, 0.2 mol) and cooled to ~5-10° C. HClO$_4$ (1.4 mL, 0.032 mol) was added drop-wise over 10 minutes followed by 2,5-dimethyl-2,5-dihydroperoxyhexyne-3 (14 g, 0.16 mol) portion wise over 1 h. The reaction mixture was warmed to 40° C. with stirring overnight. The reaction mixture was cooled to room temperature, diluted with pentane and washed with brine. The organic layer was dried over anhydrous MgSO$_4$, filtered and concentrated to afford the crude material. The product was purified by flash column chromatography 1 g of clean product. $^{13}$C-NMR δ 22.66, 24.75, 26.08, 27.48, 35.54, 74.42, 80.25, 85.82.

Reference Peroxides:

The reference peroxides were commercially available peroxides and represent the state of art of peroxides. The used peroxides are listed below.

Polymer

LDPE: Preparation of poly(ethylene-co-1,7-octadiene) (Copolymer of Ethylene Produced in a High Pressure Process)

Ethylene was compressed in a 5-stage precompressor and a 2-stage hyper compressor with intermediate cooling to reach an initial reaction pressure of ca. 2904 bar. The total compressor throughput was ca. 30 tons/hour. In the compressor area approximately 105 kg propylene/hour was added as chain transfer agent to maintain an MFR of 1.86 g/10 min. Here also 1,7-octadiene was added to the reactor in amount of ca. 62.5 kg/h. The compressed mixture was heated to approximately 159° C. in a preheating section of a front feed three-zone tubular reactor with an inner diameter of ca. 40 mm and a total length of ca. 1200 meters. A mixture of commercially available peroxide radical initiators dissolved in isododecane was injected just after the preheater in an amount sufficient for the exothermal polymerization reaction to reach peak temperature of ca. 289° C. after which it was cooled to approx 224° C. The subsequent 2nd and 3rd peak reaction temperatures were ca. 283° C. and ca. 262° C., respectively, with a cooling in between down to approximately 224° C. The reaction mixture was depressurized by a kick valve, cooled and polymer was separated from unreacted gas.

The obtained polymer had a total number of C—C carbon double bonds of 1.11/1000 C and the number of vinyl groups was 0.82 vinyl groups/1000 C. The density of the material was 921 kg/m$^3$ and MFR (2.16 kg)=1.86 g/10 min.

The above unsaturated polymer was used in testing the examples of the invention containing compounds of the invention as the crosslinking agent, comparative examples with dicumyl peroxide and other peroxides as the crosslinking agent were also tested.

Test Polymer Compositions

Wt % of peroxide is based on the amount of the polymer composition

Inventive polymer composition (Inv.comp 1): LDPE+1.5 wt % of Example 1

Inventive polymer composition (Inv.comp 2): LDPE+1.7 wt % of Example 2

Reference polymer composition 1 (Ref.comp 1): LDPE+2.0 wt % Dicumyl peroxide

Reference polymer composition 2 (Ref.comp 2): LDPE+2.0 wt % Di(2-t-butylperoxyisopropyl)benzene Reference polymer composition 3 (Ref.comp 3): LDPE+2.0 wt % t-Butyl cumyl peroxide Reference polymer composition 4 (Ref.comp 4): LDPE+2.0 wt % 2,5-Dimethyl-2,5-di(t-butylperoxy)hexyne-3

Reference polymer composition 5 (Ref.comp 5): LDPE+2.0 wt %2,5-Dimethyl-2,5-di(t-butylperoxy)hexane Gel Content Measurement The gel content was determined according to the method above and the results are shown below in Table I. In this experiment the reference polymer for gel content was prepared as the test sample of the invention, however no peroxide was added.

TABLE I

| Gel content | |
| --- | --- |
| Example | Gel content (%) |
| Ref. polymer composition without peroxide | 0 |
| Inv. Comp 1 | 82 |
| Inv. Comp 2 | 79 |

Results show the very good crosslinking performance of the compound (I) of the invention.

GC-Analysis

GC-analysis was performed as described above to evaluate the amount of formed CH$_4$. The results are presented below in Table II.

TABLE II

| GC-analysis of the CH$_4$ content of different peroxides. | |
| --- | --- |
| Example | CH$_4$ content (ppm) |
| Ref. comp 1 | 719 (gel content 93%) |
| Ref. comp 2 | 643 (gel content 89%) |
| Ref. comp 3 | 486 (gel content 86%) |
| Ref. comp 4 | 224 (gel content 86%) |
| Ref. comp 5 | 259 (gel content 86%) |
| Inv. comp 1 | 55 (gel content 82%) |
| Inv. comp 2 | 81 (gel content 79%) |

Results show that the Inv. compositions provide comparative level of crosslinking, even when used in lower amounts compared to the Ref compositions. Moreover, the methane content of Inv. compositions is markedly lower compared to ref compositions.

The invention claimed is:
1. A compound of formula (III)

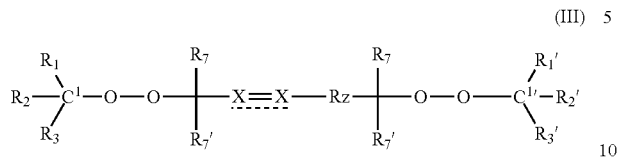

(III)

wherein
each X is CH, C or N provided that at least one X is C or CH;
the dotted line is an optionally present bond when both X groups are C;
Rz is a covalent bond or a divalent group Ry-X=X or Ry-C≡C; provided that at least one X is CH;
Ry is divalent substituted or unsubstituted saturated or partially unsaturated hydrocarbyl or substituted or unsubstituted aromatic hydrocarbyl group;
  wherein said substituted or unsubstituted saturated or partially unsaturated hydrocarbyl or aromatic hydrocarbyl optionally comprises 1 to 6 heteroatoms;
  wherein said substituted saturated or partially unsaturated hydrocarbyl or substituted aromatic hydrocarbyl comprise independently 1 to 8 substituents selected from a functional group, a saturated or partially unsaturated hydrocarbyl optionally bearing a functional group, a saturated or partially unsaturated hydrocarbyl optionally interrupted by 1 to 4 heteroatoms or aromatic hydrocarbyl optionally bearing a functional group;
$R_7$ and $R_{7'}$ can be the same or different and are independently selected from an unsubstituted saturated or partially unsaturated hydrocarbyl group;
$R_1$ and $R_{1'}$ are each independently H, substituted or unsubstituted saturated or partially unsaturated hydrocarbyl or substituted or unsubstituted aromatic hydrocarbyl;
  wherein each of said substituted or unsubstituted saturated or partially unsaturated hydrocarbyl or aromatic hydrocarbyl optionally comprises 1 to 6 heteroatoms;
  wherein said substituted saturated or partially unsaturated hydrocarbyl or substituted aromatic hydrocarbyl comprise independently 1 to 4 substituents selected from a functional group, a saturated or partially unsaturated hydrocarbyl optionally bearing a functional group or aromatic hydrocarbyl optionally bearing a functional group;
$R_2$, $R_{2'}$, $R_3$ and $R_{3'}$ are each independently H, substituted or unsubstituted saturated or partially unsaturated hydrocarbyl or substituted or unsubstituted aromatic hydrocarbyl;
  wherein each of said substituted or unsubstituted saturated or partially unsaturated hydrocarbyl or aromatic hydrocarbyl optionally comprises 1 to 6 heteroatoms;
  wherein said substituted saturated or partially unsaturated hydrocarbyl or substituted aromatic hydrocarbyl optionally comprise independently 1 to 4 substituents selected from a functional group or a saturated or partially unsaturated hydrocarbyl optionally bearing a functional group or aromatic hydrocarbyl optionally bearing a functional group; or
$R_2$ and $R_3$ together with the carbon atom ($C^1$) to which they are attached form an unsubstituted or substituted saturated or partially unsaturated carbocyclic ring moiety of 3 to 14 C-atoms; an unsubstituted or substituted saturated or partially unsaturated heteroring moiety of 3 to 14 ring atoms comprising 1 to 6 heteroatoms, selected from O, N, P, S or Si; or an unsubstituted or substituted aromatic ring moiety of 3 to 14 C-atoms, optionally comprising 1 to 4 heteroatoms;
  wherein said substituted carbocyclic ring, heteroring or aromatic ring system comprises 1 to 4 substituents selected independently from a functional group, or a saturated or partially unsaturated hydrocarbyl optionally bearing a functional group, or aromatic hydrocarbyl optionally bearing a functional group; or
$R_{2'}$ and $R_{3'}$ together with the carbon atom ($C^{1'}$) to which they are attached form an unsubstituted or substituted saturated or partially unsaturated carbocyclic ring moiety of 3 to 14 C-atoms; an unsubstituted or substituted saturated or partially unsaturated heteroring moiety of 3 to 14 ring atoms comprising 1 to 6 heteroatoms, selected from O, N, P, S or Si; or unsubstituted or substituted aromatic ring moiety of 3 to 14 C-atoms optionally comprising 1 to 4 heteroatoms;
  wherein said substituted carbocyclic ring, heteroring or aromatic ring system comprises 1 to 4 substituents selected independently from a functional group or a saturated or partially unsaturated hydrocarbyl optionally bearing a functional group or aromatic hydrocarbyl optionally bearing a functional group;
with a proviso that at least two of $R_1$, $R_2$ and $R_3$ are other than H or methyl; or that at least one of $R_1$, $R_2$ and $R_3$ is an alkenyl or alkynyl group;
or functional derivative thereof.

2. A compound as claimed in claim 1, wherein $R_7$ and $R_{7'}$ are methyl.

3. A compound as claimed in claim 1 of formula (IV) or (V)

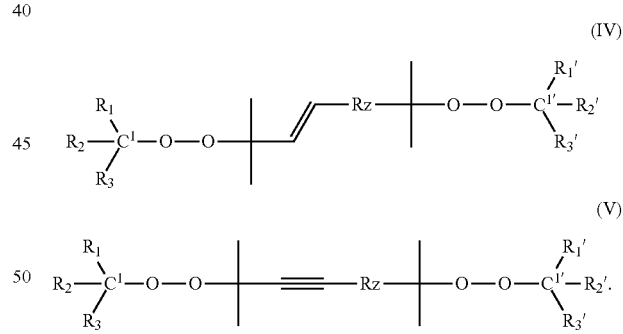

4. A compound as claimed in claim 1, wherein the groups $C^1R_{1-3}$ and $C^{1'}R_{1'-3'}$ are the same.

5. A compound as claimed in claim 1 of formula (VI) or (VIII)

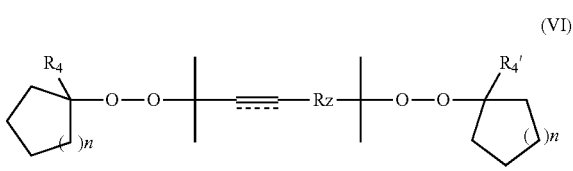

(VI)

-continued

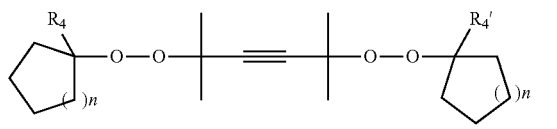

(VII)

wherein n is 0 to 3, $R_4$ and $R_{4'}$ each independently represent a branched or straight chain alkyl group having 1 to 30 carbon atoms;

wherein one or both ring systems independently are unsubstituted or optionally substituted by 1 to 4 substituents Z and Z is selected from a saturated or partially unsaturated (C1-C30)hydrocarbyl, a functional group, a saturated or partially unsaturated (C1-C30)hydrocarbyl which optionally bears a functional group as defined above, or from an aromatic hydrocarbyl, which optionally bears a functional group.

6. A compound as claimed in claim 5 wherein the dotted bond is present thus forming a triple bond.

7. A compound as claimed in claim 1 wherein Rz is a covalent bond.

8. A polymer composition comprising
   A) a polymer and
   B) a compound of formula (III) as claimed claim 1.

9. A polymer composition as claimed in claim 8 wherein said polymer is a polyolefin.

10. A modified polymer composition in which the polymer composition of claim 8 is cross-linked by initiating a radical reaction in the polymer composition.

11. A crosslinkable cable which comprises a conductor which is surrounded by one or more layers, wherein the at least one layer comprises the polymer composition as claimed in claim 8.

12. A crosslinkable cable as defined in claim 11, which is selected from any of the following cables:
    a low voltage cable comprising a conductor surrounded by an insulation layer and optionally a jacketing layer, wherein at least one layer, comprises the polymer composition; or
    a power cable comprising an electrical conductor surrounded by one or more layers comprising at least an inner semiconductive layer, insulation layer and an outer semiconductive layer, in that order, and optionally surrounded by a jacketing layer, wherein at least one of said layers comprises, the polymer composition.

13. A process for producing a crosslinkable cable comprising applying one or more layers comprising a polymer composition on a conductor wherein at least one layer comprises a polymer composition as claimed in claim 8.

14. A process as claimed in claim 13 for crosslinking a cable by radical reaction, comprising:
    applying one or more layers comprising the polymer composition on a conductor, and
    crosslinking by radical reaction said at least one layer; optionally
    subjecting the crosslinked cable thus obtained to a cooling step, wherein said crosslinked cable is cooled under non-pressurized or pressurized conditions.

15. A crosslinked cable prepared by the process as defined in claim 14.

* * * * *